(12) United States Patent
Wang et al.

(10) Patent No.: US 7,618,962 B2
(45) Date of Patent: Nov. 17, 2009

(54) PYRAZOLYL SUBSTITUTED XANTHINES

(75) Inventors: Guoquan Wang, Charlottesville, VA (US); Jayson M. Rieger, Charlottesville, VA (US); Robert D. Thompson, Charlottesville, VA (US)

(73) Assignee: PGX Health, LLC, Newton, MA (US)

( * ) Notice: Subject to any disclaimer, the term of this patent is extended or adjusted under 35 U.S.C. 154(b) by 462 days.

(21) Appl. No.: 11/362,393

(22) Filed: Feb. 27, 2006

(65) Prior Publication Data

US 2007/0066631 A1 Mar. 22, 2007

Related U.S. Application Data

(60) Provisional application No. 60/656,105, filed on Feb. 25, 2005.

(51) Int. Cl.
*C07D 473/04* (2006.01)
*C07D 473/06* (2006.01)
*A61K 31/522* (2006.01)
*A61P 11/06* (2006.01)
*C07D 403/12* (2006.01)

(52) U.S. Cl. ............... 514/234.2; 544/118; 544/269; 544/270; 544/310; 514/263.2; 514/263.21; 514/263.22

(58) Field of Classification Search ............... 544/118, 544/269, 270; 514/234.2, 263.2, 263.21, 514/263.22
See application file for complete search history.

(56) References Cited

U.S. PATENT DOCUMENTS

| | | | |
|---|---|---|---|
| 6,825,349 B2 * | 11/2004 | Kalla et al. | 544/267 |
| 7,205,403 B2 * | 4/2007 | Baraldi et al. | 544/118 |
| 7,304,070 B2 * | 12/2007 | Kalla et al. | 514/263.2 |
| 7,342,006 B2 * | 3/2008 | Wang et al. | 514/211.08 |
| 2003/0229106 A1 * | 12/2003 | Kalla et al. | 514/263.2 |
| 2004/0192708 A1 * | 9/2004 | Dunten et al. | 514/263.22 |
| 2005/0065341 A1 * | 3/2005 | Wang et al. | 544/269 |
| 2006/0058322 A1 * | 3/2006 | Zeng et al. | 514/263.2 |
| 2006/0159627 A1 * | 7/2006 | Zeng et al. | 424/45 |
| 2007/0072843 A1 * | 3/2007 | Wang et al. | 514/217.06 |
| 2007/0105821 A1 * | 5/2007 | Wang et al. | 514/81 |
| 2007/0249598 A1 * | 10/2007 | Wang et al. | 514/234.2 |
| 2008/0004292 A1 * | 1/2008 | Wang et al. | 514/263.22 |
| 2008/0200456 A1 * | 8/2008 | Wang et al. | 514/234.2 |

FOREIGN PATENT DOCUMENTS

WO WO03422214 * 5/2003
WO WO03063800 A2 * 8/2003

OTHER PUBLICATIONS

Sekine, Chem. Pharm Bull. 37 (8), 1987-1989 (1990).*

* cited by examiner

*Primary Examiner*—Mark L Berch

(57) ABSTRACT

The present invention provides compounds and pharmaceutical compositions that are substituted pyridyl-linked-xanthines of formula I

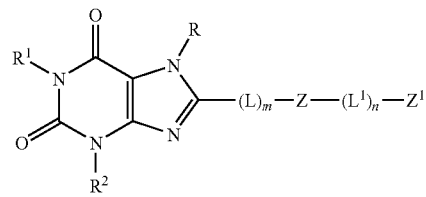

which are selective antagonists of $A_{2B}$ adenosine receptors (ARs). These compounds and compositions are useful as pharmaceutical agents.

59 Claims, No Drawings

PYRAZOLYL SUBSTITUTED XANTHINES

This application claims priority to application Ser. No. 60/656,105, filed Feb. 25, 2005, the contents of which are hereby incorporated by reference in their entirety.

FIELD OF THE INVENTION

The present invention relates to compounds and pharmaceutical compositions that are selective antagonists of $A_{2B}$ adenosine receptors (ARs). These compounds and compositions are useful as pharmaceutical agents.

BACKGROUND OF THE INVENTION

The alkylxanthine theophylline (compound A) is a weak non-selective

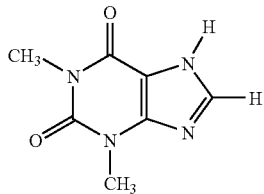

A adenosine antagonist (See Linden, J., et al., *Cardiovascular Biology of Purines*, eds. G. Burnstock, et al., 1998, pp 1-20) that is useful therapeutically for the treatment of asthma. However, its use is associated with unpleasant side effects, such as insomnia and diuresis. In recent years the use of theophylline as a bronchodilator for relief of asthma, has been supplanted by drugs of other classes, i.e., selective $\beta_2$-adrenergic agonists, corticosteroids, and recently leukotriene antagonists. These compounds also have limitations, and therefore the development of a theophylline-like drug with reduced side effects is still desirable.

It has been recognized that theophylline, and its closely related analogue caffeine, block endogenous adenosine acting as a local modulator of adenosine receptors in the brain and other organs when administered at therapeutically useful doses. Adenosine activates four subtypes of G protein-coupled adenosine receptors (ARs), $A_1/A_{2A}/A_{2B}/A_3$. Enprofylline, (compound B), is another example of a xanthine

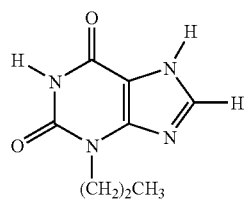

B that has been reported to block $A_{2B}$ adenosine receptors and is used to treat asthma. However, this compound only weakly blocks $A_1$, $A_{2A}$ and $A_3$ adenosine receptors. It has also been shown by LaNoue et al (U.S. Pat. No. 6,060,481) that selective adenosine $A_{2B}$ antagonists are useful for improving insulin sensitivity in a patient.

It has been reported that therapeutic concentrations of theophylline or enprofylline block human $A_{2B}$ receptors, and it has been proposed that antagonists selective for this subtype may have potential use as antiasthmatic agents. (See Feoktistov, I., et al., *Pharmacol. Rev.* 1997, 49, 381-402; and Robeva, A. S., *Drug Dev. Res.* 1996, 39, 243-252). Enprofylline has a reported $K_i$ value of 7 µM and is somewhat selective in binding to human $A_{2B}$ ARs. (See Robeva, A. S., *Drug Dev. Res.* 1996, 39, 243-252 and Linden, J., et al., *Mol. Pharmacol.* 1999, 56, 705-713). $A_{2B}$ ARs are expressed in some mast cells, such as the BR line of canine mastocytoma cells, which appear to be responsible for triggering acute $Ca^{2+}$ mobilization and degranulation. (See Auchampach, J. A., *Mol. Pharmacol.* 1997, 52, 846-860 and Forsyth, P., et al., *Inflamm. Res.* 1999, 48, 301-307). $A_{2B}$ ARs also trigger $Ca^{2+}$ mobilization, and participate in a delayed IL8 release from human HMC-1 mast cells. Other functions associated with the $A_{2B}$ AR are the control of cell growth and gene expression, (See Neary, J., et al., *Trends Neurosci.* 1996, 19, 13-18) endothelial-dependent vasodilation (See Martin, P. L., *J. Pharmacol. Exp. Ther.* 1993, 265, 248-253), and fluid secretion from intestinal epithelia. (See Strohmeier, G. R., *J. Biol. Chem.* 1995, 270, 2387-2394). Adenosine acting through $A_{2B}$ ARs also has been reported to stimulate chloride permeability in cells expressing the cystic fibrosis transport regulator. (See Clancy, J. P., *Am. J. Physiol.* 1999, 276, C361-C369.)

Recently Linden et al. (U.S. Pat. No. 6,545,002) have described a new group of compounds and pharmaceutical compositions that are selective antagonists of $A_{2B}$ adenosine receptors (ARs).

Although adenosine receptor subtype-selective probes are available for the $A_1$, $A_{2A}$, and $A_3$ ARs, only a few selective antagonists and no selective agonists are known for the $A_{2B}$ receptor. Therefore, a continuing need exists for compounds that are selective $A_{2B}$ receptor antagonists.

SUMMARY OF THE INVENTION

The present invention provides compounds that act as antagonists of $A_{2B}$ adenosine receptors. Accordingly, the present invention provides a compound of formula I:

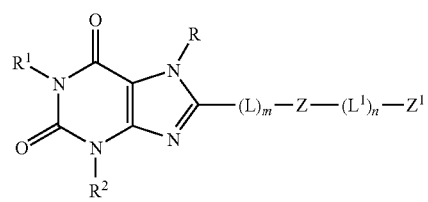

I wherein:
R is hydrogen or is selected from the group consisting of $(C_{1-5})$alkyl, halo$(C_{1-8})$alkyl, $(C_{3-8})$cycloalkyl, $(C_{3-8})$cycloalkyl$(C_{1-8})$alkyl-, $(C_{3-5})$alkenyl and $(C_{3-5})$alkynyl, each optionally substituted or unsubstituted;

$R^1$ and $R^2$ are each independently selected from the group consisting of hydrogen, $(C_{1-8})$alkyl, halo$(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-;

L and $L^1$ are each independently a linker comprising 1, 2, 3 or 4 linking atoms selected from the group consisting of carbon, nitrogen, oxygen, sulfur and phosphorus, provided that L and $L^1$ are not N, O, S or P when they are directly attached to a ring heteroatom;

Z is a 5-14 member substituted or unsubstituted heteroaryl ring;

$Z^1$ is a 5-14 member substituted or unsubstituted aryl or heteroaryl ring;

where m is 0, 1 or 2; n is 0, 1 or 2; or a pharmaceutically acceptable salt thereof.

The invention also provides pharmaceutically acceptable salts of a compound of formula I. The invention also provides a pharmaceutical composition comprising a compound of formula I, or a pharmaceutically acceptable salt thereof, in combination with a pharmaceutically acceptable diluent or carrier.

Additionally, the invention provides a therapeutic method for preventing or treating a pathological condition or symptom in a mammal, such as a human, wherein the activity, i.e., over-activity, of adenosine $A_{2B}$ receptors is implicated in one or more symptoms of the pathology, and antagonism (i.e., partial or complete blocking) of the receptor activity is desired to ameliorate said symptoms. Such diseases or conditions include, but are not limited to, asthma, allergies, allergic diseases (e.g. allergic rhinitis and sinusitis), autoimmune diseases (e.g. lupus), diarrheal diseases, insulin resistance, diabetes, prevention of mast cell degranulation associated with ischemia/reperfusion injuries, heart attack, inhibition of angiogenesis in neoplastic tissues, and inhibition of angiogenesis in diabetic retinopathy or hyperbaric oxygen-induced retinopathy. The invention also includes a method for treating asthma, diarrheal diseases, insulin resistance, diabetes, inhibition of angiogenesis in neoplastic tissues, and inhibition of angiogenesis in diabetic retinopathy or hyperbaric oxygen-induced retinopathy in a mammal, (e.g., a human) comprising administering to the mammal in need of such therapy, an effective amount of at least one compound of formula I or pharmaceutically acceptable salt(s) thereof.

The invention provides a compound of formula I for use in medical therapy, preferably for use in treating diseases or conditions associated with deleterious $A_{2B}$ receptor activation or activity, including asthma, diarrheal diseases, insulin resistance, diabetes, ischemic/reperfusion injury, inhibition of angiogenesis in neoplastic tissues, and inhibition of angiogenesis in diabetic retinopathy or hyperbaric oxygen-induced retinopathy.

The invention also provides the use of a compound of formula I for the manufacture of a medicament for the treatment of a pathological condition or symptom in a mammal, such as a human, which is associated with deleterious $A_{2B}$ receptor activation or activity, including the above-referenced diseases or pathologies.

The invention also includes a method comprising contacting a compound of formula I, optionally having a radioactive isotope (radionuclide), such as, for example, tritium, radioactive iodine (for example, $^{125}$I for binding assays or $^{123}$I for spectral imaging) and the like, with target $A_{2B}$ adenosine receptor sites comprising said receptors, in vivo or in vitro, so as to bind to said receptors. Cell membranes comprising bound $A_{2B}$ adenosine receptor sites can be used to measure the selectivity of test compounds for adenosine receptor subtypes or can be used as a tool to identify potential therapeutic agents for the treatment of diseases or conditions associated with $A_{2B}$-receptor mediation, by contacting said agents with said radioligands and receptors, and measuring the extent of displacement of the radioligand and/or binding of the agent.

DETAILED DESCRIPTION OF THE INVENTION

Applicants have discovered that compounds of the invention having formula I, can be useful for the treatment diseases or conditions associated with deleterious $A_{2B}$ receptor activation or activity.

The following definitions are used, unless otherwise described:

"Halo" means fluoro, chloro, bromo, or iodo.

A "haloalkyl" such as a "halo($C_{1-8}$)alkyl" includes the compound that is a mono-halohalo($C_{1-8}$)alkyl, dihalo($C_{1-8}$)alkyl, tri-halo($C_{1-8}$)alkyl, perhaloalkyl, and the like, and for example, includes such groups such as $CF_3$—, $CF_3CF_2$—, and the like, unless otherwise indicated.

"Alkyl", "alkoxy", "alkenyl", "alkynyl", etc. denote both straight and branched groups; but reference to an individual radical such as "propyl" embraces only the straight chain radical, a branched chain isomer such as "isopropyl" being specifically referred to. "$C_{X-Y}$alkyl" is used where X and Y indicate the number of carbon atoms in the chain. For example, $C_{1-4}$alkyl include alkyl groups that have a chain between 1 and 4 carbon atoms (e.g. methyl, ethyl, propyl, isopropyl, butyl, sec-butyl, isobutyl, etc.).

"Amino" denotes a nitrogen moiety having two substituents attached to the nitrogen atom. Examples of an amino group include —$NH_2$, —$NH_2NH_2$, —$NH_2NHCH_3$, —$NHCH_2CH_3$, and the like. The two substituents attached to the nitrogen atom may be combined with the nitrogen to form a saturated or unsaturated ring. The amino group may be derivatized with other functional groups such as amino protecting groups that are well known in the art such as those described in *Protective Groups in Organic Synthesis*, T. W. Greene, John Wiley & Sons, New York, 1999 or the latest edition, and related texts.

"Aryl" denotes a phenyl radical or an ortho-fused bicyclic carbocyclic radical having about nine to ten ring atoms in which at least one ring is aromatic.

"Arylalkyl" or "($C_{6-10}$)aryl($C_{1-8}$)alkyl-" refer to a group of the formula aryl($C_{1-8}$)alkyl-, where aryl and ($C_{1-8}$)alkyl are as defined herein. As used conventionally in the art, a compound group, that is, a group having two or more moieties such as an "arylalkyl" or "($C_{6-10}$)aryl($C_{1-8}$)alkyl-", is a group or a substituent that is attached at the last listed of the compound group. For the examples above, the attachment is at the second of the compound group, viz, at the alkyl group; and such group may also be represented as "arylalkyl-" or "($C_{6-10}$)aryl($C_{1-8}$)alkyl-".

"Carbonyl" as used herein is the radical group "—CO—" and may include various carbonyl derivatives including carboxyls, carboxylate salts, carboxylate esters, thioesters, ketones, amides, carbamates and the like.

"Heterocycle" encompasses a cyclic radical attached or linked via a nitrogen or carbon ring atom of a monocyclic, fused-bicyclic, or bridged-bicyclic, saturated or unsaturated, ring system containing 5-10 ring atoms and preferably from 5-6 ring atoms, consisting of carbon and one, two, three or four heteroatoms including, for example, non-peroxide oxy (—O—), thio (—S—), sulfinyl (—SO—), sulfonyl (—S(O)$_2$—), amine —N(R)—, —N(O)—, —N═, phosphorus (—P—), —P(O)—, etc. . . . , wherein the group R is as defined herein, and optionally containing 1-3 double bonds (e.g., —CH═CH— or —CH═N—). Fully unsaturated heterocycles may also be defined as "heteroaryls." Heterocycle includes, for example, tetrahydrofuryl, dihydrofuryl, tetrahydroimidazolyl, azanorbornyl, pyrrolidyl, piperidyl, piperizyl, morpholinyl, azepinyl, 1,3-diazepinyl, 1,3-benzodiazepinyl, 1,4-diazepinyl, 1,4-benzodiazepinyl, 1,5-diazepinyl, 1,5-benzodiazepino and the like.

"Heteroaryl" encompasses a radical attached via a ring atom of a monocyclic or bicyclic aromatic ring containing 5-14 ring atoms, such as a monocyclic containing from 5-6 ring atoms, comprising carbon and one, two, three or four heteroatoms including, for example, non-peroxide oxy (—O—), thio (—S—), sulfinyl (—SO—), sulfonyl (—S(O)$_2$—), amine —N(R—), —N(O)—, —N═, etc...., wherein the group R is as defined herein. Bicyclic or tricyclic heteroaryls include, but are not limited to, those derived from benzo[b]furan, benzo[b]thiophene, benzimidazole, imidazo [4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, pteridine, purine, carbazole, acridine and the like. Preferred heteroaryl groups include imidazolyl, triazolyl, triazinyl, oxazoyl, isoxazoyl, thiazolyl, isothiazolyl, thiodiazolyl, pyrrolyl, pyrazolyl, pyrazinyl, tetrazolyl, pyridinyl, pyrimidinyl, indolyl, isoquinolyl, quinolyl and the like.

"Isomer" as used herein means any compound having an identical molecular formula but differing in the nature or sequence of bonding of its atoms or in the arrangement of its atoms in space. Isomers that differ in the arrangement of their atoms in space are termed "stereoisomers" that may be enantiomers or diastereomers. A carbon atom bonded to four nonidentical substituents is termed a "chiral center" and such compounds containing a chiral center may be termed a chiral compound. Conventions for stereochemical nomenclature, methods for the determination of stereochemistry and the separation of stereoisomers are well known in the art from standard texts such as "Advanced Organic Chemistry", 4th edition, March, Jerry, John Wiley & Sons, New York, 1992, and "Introduction to Organic Chemistry", latest edition, A. Streitwieser, Jr. & C. H. Heathcock, MacMillan Publishing Co., Inc. New York.

The present invention is intended to encompass all pharmaceutically acceptable ionized forms (e.g., salts) and solvates (e.g., hydrates) of the compounds, regardless of whether such forms and solvates are specified, as it is well known in the art that pharmaceutical agents in an ionized or solvated form may be used. Unless a particular stereochemistry is specified, recitation of a compound is intended to encompass all possible stereoisomers (e.g., enantiomers or diastereomers), independent of whether the compound is present as an individual isomer or a mixture of isomers. A recitation of a compound is intended to include all possible resonance forms and isomers. Claims to the compound of the present invention are intended to encompass the compound and all pharmaceutically acceptable ionized forms and solvates, all possible stereoisomers, resonance forms and isomers, unless otherwise specifically specified.

"Pharmaceutically acceptable salts" means salts of the compounds of the present invention which are pharmaceutically acceptable and which have the desired pharmacological activity. Such salts include acid addition salts formed with inorganic acids such as hydrochloric acid, hydrobromic acid, sulfuric acid, nitric acid, phosphoric acid, and the like. The salt may also be formed with organic acids including acetic acid, propionic acid, hexanoic acid, heptanoic acid, glycolic acid, pyruvic acid, lactic acid, malonic acid, succinic acid, malic acid, maleic acid, fumaric acid, tartatic acid, citric acid, benzoic acid, gluconic acid, glutamic acid, and the like.

Prodrugs of the compounds of the present invention may also be administered. As is known in the art, prodrugs are altered in vivo and become a compound of the present invention. All standard methods of using the compounds of the present invention are intended, whether or not prodrug delivery is specified, to encompass the administration of a prodrug that is converted in vivo to a compound according to the present invention. Also, some compounds of the present invention may be altered in vivo prior to being biologically active as selective antagonists of $A_{2B}$ adenosine receptors, and therefore, may themselves be prodrugs for another compound.

"Thio" as used as a substituent herein, means the group —S—, —SO—, —SO$_2$—, —SO$_3$— and their derivatives including, for example, —S-alkyl, —S-aryl, —S-heteroaryl, —SO-aryl, —SO-heteroaryl, —SO—NR'R", —SO$_2$NR'R" and the like, wherein R' and R" are as defined herein.

As is recognized by one of ordinary skill in the art, the imidazole ring of the compounds of the present invention may exist in isomeric forms or as isomers, and thus are also included within the scope of the invention. For example, the isomers are represented as the structures (Ia) and (Ib):

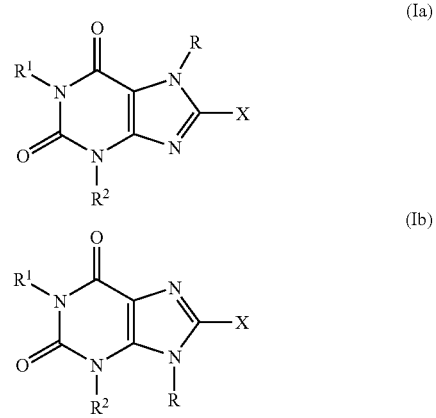

By naming or referring to one compound I, for example, it is understood for the purposes of the present application that the isomers (Ia) and (Ib) are also intended, unless specifically indicated otherwise. Similarly, by referring to compound (Ia), it is understood for the purposes of the present application that the isomers I and (Ib) are also intended. The same holds true for references to isomer (Ib).

"Optional" or "optionally" mean that the subsequently described event or condition may, but need not, occur, and that the description includes instances where the event or condition occurs and instances in which it does not. For example, "optionally substituted" means that the named substituent may be present but need not be present, and the description includes situations where the named substituent is included and situations where the named substituent is not included.

The terms "include", "for example", "such as", and the like are used illustratively and are not intended to limit the present invention.

The indefinite articles "a" and "an" mean "at least one" or "one or more" when used in this application, including the claims, unless specifically indicated otherwise.

It will be appreciated by those skilled in the art that compounds of the invention having a chiral center may exist in and be isolated in optically active, and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine, for example, anti-tumor activity, herbicidal activity, or other therapeutic activity using the standard tests described herein, or using other similar tests which are well known in the art.

Specific and preferred values listed below for radicals, substituents, and ranges, are for illustration only; they do not exclude other defined values or other values within defined ranges for the radicals and substituents.

Specifically, $(C_{1-9})$alkyl can be methyl, ethyl, n-propyl, isopropyl, n-butyl, iso-butyl, sec-butyl, tert-butyl, n-pentyl, isopentyl, 3-pentyl, n-hexyl, n-heptyl, n-octyl or the branched $(C_{3-8})$alkyl; $(C_{2-8})$alkenyl can be vinyl, 1-propenyl, 2-propenyl (allyl), 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 3-heptenyl, 1-octenyl, 2-octenyl, 3-octenyl, 4-octenyl or the branched $(C_{3-8})$alkenyl; $(C_{3-8})$ alkenyl can be 2-propenyl (allyl), 2-butenyl, 3-butenyl, 2-pentenyl, 3-pentenyl, 1-hexenyl, 2-hexenyl, 3-hexenyl, 2-heptenyl, 3-heptenyl, 2-octenyl, 3-octenyl, 4-octenyl, or the branched $(C_{3-8})$alkenyl; $(C_{2-8})$alkynyl can be ethynyl, 1-propynyl, 2-propynyl (propargyl), 1-butynyl, 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or the branched $(C_{3-8})$alkynyl; $(C_{3-8})$alkynyl can be 2-propynyl (propargyl), 2-butynyl, 3-butynyl, 1-pentynyl, 2-pentynyl, 3-pentynyl, 1-hexynyl, 2-hexynyl, 3-hexynyl, 1-heptynyl, 2-heptynyl, 3-heptynyl, 1-octynyl, 2-octynyl, 3-octynyl, 4-octynyl, or the branched $(C_{3-8})$alkynyl; $(C_{1-8})$alkoxy can be methoxy, ethoxy, n-propoxy, isopropoxy, n-butoxy, iso-butoxy, sec-butoxy, tert-butoxy, pentoxy, 3-pentoxy, n-hexyloxy, n-heptyloxy, n-octyloxy, or the branched $(C_{3-8})$alkoxy; halo$(C_{1-8})$ alkyl can be iodomethyl, bromomethyl, chloromethyl, fluoromethyl, trifluoromethyl, 2-chloroethyl, 2-bromoethyl, 2-fluoroethyl, 3-fluoropropyl, 2,2,2-trifluoroethyl, pentafluoroethyl, or the branched halo$(C_{3-8})$alkyl; $(C_{3-8})$cycloalkyl can be cyclopropyl, cyclobutyl, cyclopentyl, cyclohexyl, cycloheptyl or cyclooctyl; $(C_{3-8})$cycloalkyl$(C_{1-8})$alkyl- can be cyclopropylmethyl, cyclobutylmethyl, cyclopentylmethyl, cyclohexylmethyl, 2-cyclopropylethyl, 2-cyclobutylethyl, 2-cyclopentylethyl or 2-cyclohexylethyl; $(C_{6-10})$aryl can be phenyl, indenyl or naphthyl.

A "substituted" group, such as a substituted alkyl group or a substituted aryl group, means that one or more of the hydrogen atom on the alkyl or aryl group is replaced by the specified substituent or substituents as known in the art.

Arylalkyl can be, for example, phenylethyl, benzyl, 2-phenylpropyl, 3-phenylpropyl, 2-naphthylmethyl or 3-naphthylmethyl; and heteroaryl can be, for example, imidazolyl, triazolyl, triazinyl, oxazoyl, isoxazoyl, thiazolyl, isothiazoyl, pyrrolyl, pyrazinyl, tetrazolyl, pyridyl, pyrimidinyl, indolyl, isoquinolyl, quinolyl, or an oxide thereof.

The $(C_{1-8})$alkyl groups can be methyl, ethyl, propyl, butyl, pentyl, hexyl, heptyl, and octyl; alkenyl groups may include, for example, ethenyl, propenyl, butenyl, pentenyl, and hexenyl.

Specific cycloalkyl groups are cyclopropyl, cyclobutyl, cyclopentyl, and cyclohexyl, each unsubstituted or substituted.

Specific cycloalkylalkyl groups include, for example, cyclopropylmethyl, cyclobutylmethyl, cyclopropylethyl, cyclopentylmethyl, cyclohexylmethyl, 2-cyclopentylethyl and 2-cyclohexylethyl, each unsubstituted or substituted.

ASPECTS OF THE INVENTION

In one aspect of the invention, there is provided a compound of formula I:

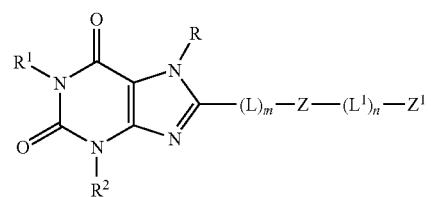

wherein:
R is hydrogen or is selected from the group consisting of $(C_{1-5})$alkyl, halo$(C_{1-8})$alkyl, $(C_{3-8})$cycloalkyl, $(C_{3-8})$cycloalkyl$(C_{1-5})$alkyl-, $(C_{3-5})$alkenyl and $(C_{3-5})$alkynyl, each substituted or unsubstituted;

$R^1$ and $R^2$ are each independently selected from the group consisting of hydrogen, $(C_{1-8})$alkyl, halo$(C_{1-8})$alkyl, $(C_{3-8})$alkenyl, $(C_{3-5})$alkynyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-;

L and $L^1$ are each independently a linker comprising 1, 2, 3 or 4 linking atoms selected from the group consisting of carbon, nitrogen, oxygen, sulfur and phosphorus, provided that L and $L^1$ are not N, O, S or P when they are directly attached to a ring heteroatom;

Z is a 5-14 member substituted or unsubstituted heteroaryl ring;

$Z^1$ is a 5-14 member substituted or unsubstituted aryl or heteroaryl;

where m is 0, 1 or 2; n is 0, 1 or 2;

or a pharmaceutically acceptable salt thereof, optionally in the form of a single stereoisomer or mixture of stereoisomers thereof.

In one aspect of the invention, there is provided a pharmaceutical composition comprising: (a) a therapeutically effective amount of a compound described above; and (b) a pharmaceutically acceptable excipient. In another aspect, there is provided a pharmaceutical composition comprising: (a) a therapeutically effective amount of a compound of the above; and (b) a pharmaceutically acceptable excipient.

In one aspect of the invention, there is provided a therapeutic method for preventing or treating a pathological condition or symptom in a mammal, wherein the activity of adenosine $A_{2B}$ receptors is implicated and antagonism of its action is desired comprising administering to the mammal an effective amount of a compound of the present invention. In another aspect of the invention, there is provided a method for treating asthma, allergies, allergic diseases or an autoimmune disease comprising administering an effective amount of a compound of the present invention to a mammal in need of such treatment.

In yet another aspect of the invention, there is provided a method for treating diarrheal diseases, insulin resistance, diabetes, cancer, ischemia/reprefusion injuries, diabetic retinopathy or hyperbaric oxygen-induced retinopathy, comprising administering an effective amount of a compound of the present invention or a pharmaceutically acceptable salt thereof to a mammal in need of such treatment. In yet another aspect, there is provided a therapeutic method for preventing or treating a pathological condition or symptom in a mammal, wherein the activity of adenosine $A_{2B}$ receptors is implicated and antagonism of its action is desired comprising administering to the mammal an effective amount of a compound of the present invention.

In another aspect of the invention, there is provided the compound of the present invention for use in medical therapy. In another aspect, there is provided a use of a compound of the invention, for the manufacture of a medicament useful for the treatment of a disease in a mammal, such as a human.

It is understood that any aspect or feature of the present invention whether characterized as preferred or not characterized as preferred may be combined with any other aspect or feature of the invention, whether such other feature is characterized as preferred or not characterized as preferred. For example, an aspect or feature described as preferred, for example a particular R group, or a specific $R^1$ group for a particular compound of the formula I (for example, where $R^1$ is hydrogen, $(C_{1-5})$alkyl, halo$(C_{1-8})$alkyl, $(C_{3-5})$alkenyl, or $(C_{3-5})$alkynyl) may be combined with any other groups such as $R^2$, X, Z, $Z^1$ etc. . . . to form a compound of the invention having a different combination of substituents without deviating from the present invention.

The compounds of the invention demonstrate improved receptor selectivity compared to compounds that previously have been described. The compounds also have greatly increased solubility under physiological conditions, which further enhances their usefulness as pharmaceutical agents. In particular, it has been found that compounds having a cyclopropyl group at the 1-position of the xanthine ring unexpectedly have a significantly increased solubility compared to isomeric compounds. Accordingly, the compounds of the present invention advantageously contain a 1-cyclopropyl moiety in the xanthine ring, although the skilled artisan will recognize that the invention also encompasses compounds having other moieties at this position.

Synthesis of the Compounds of Formula I.

The compounds of Formula I can be prepared by the general method described in Reaction Scheme 1.

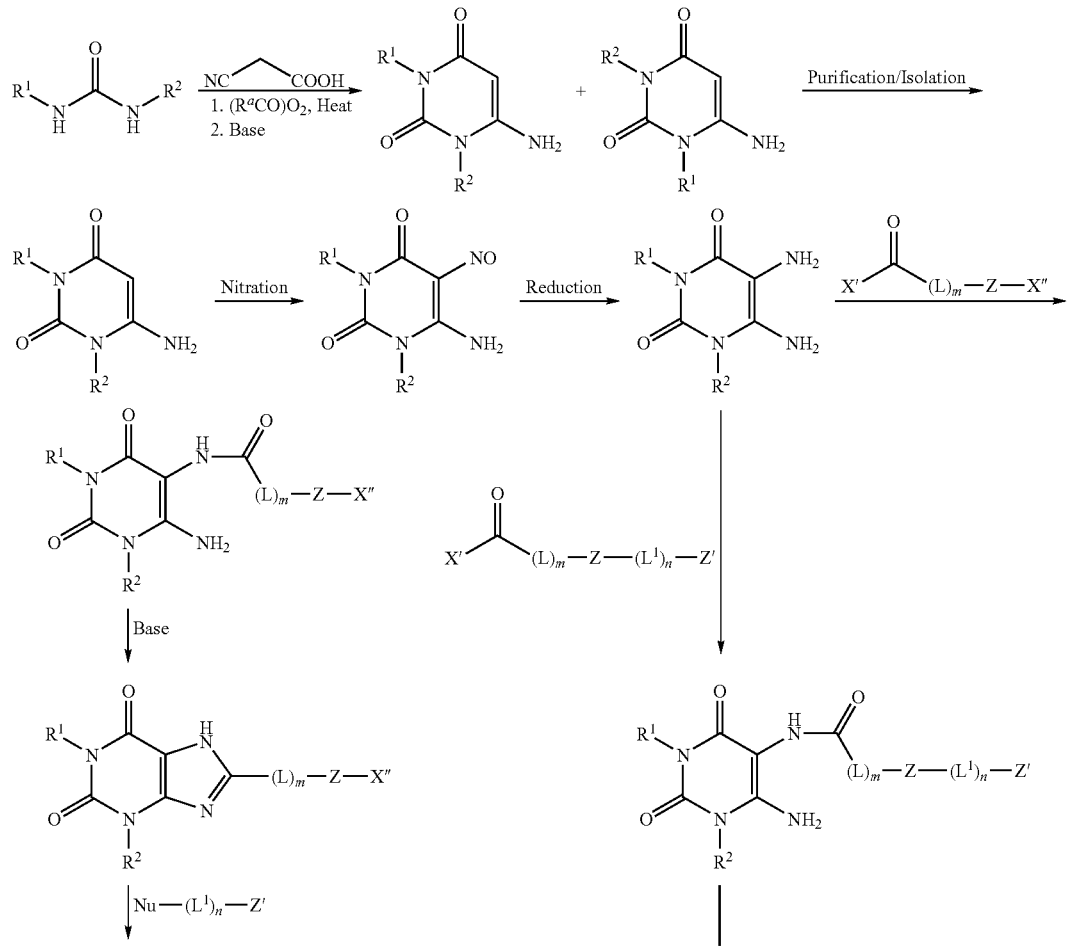

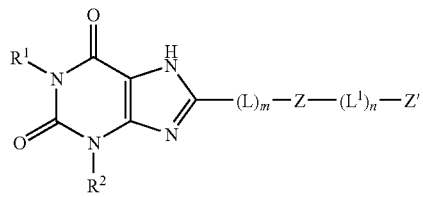

In Reaction Scheme 2, a bis-substituted urea, such as the asymmetrically substituted urea, may be prepared by the condensation of an amine with an isocyanate. Where such asymmetrically substituted urea such as a compound wherein $R^1$ is cyclopropyl and $R^2$ is an alkyl such as a propyl group is desired, for example, the condensation of 1-cyclopropylamine with N-propyl-isocyanate affords the urea. The nature of the substitution on the urea nitrogen atoms, which ultimately corresponds to the N-1 and N-3 substituents of the xanthine derivative, will be determined by the nature of the amine and isocyanate employed in the condensation reaction. The condensation reaction may be performed in a polar or non-polar aprotic solvent at about $-25°$ C. to about $50°$ C., depending the reactivities of the amine and the isocyanate reactants. Preferably, the reaction is performed in a hydrocarbon solvent such as toluene, and at a reaction temperature of about $0°$ C. to about $25°$ C. until the reaction is deemed complete. The product may be isolated by filtration and isolated in the usual way. Where further purification is desired, the product may be purified by crystallization or by chromatography, such as column chromatography.

REACTION SCHEME 2

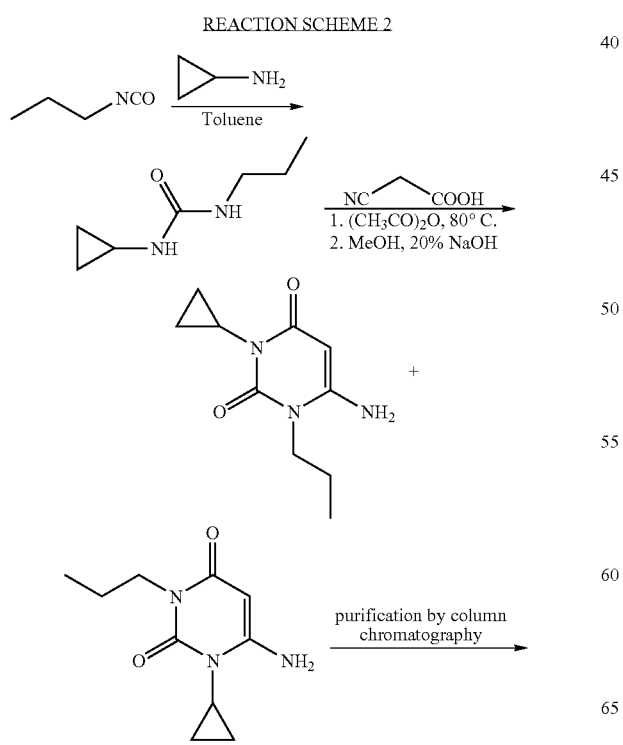

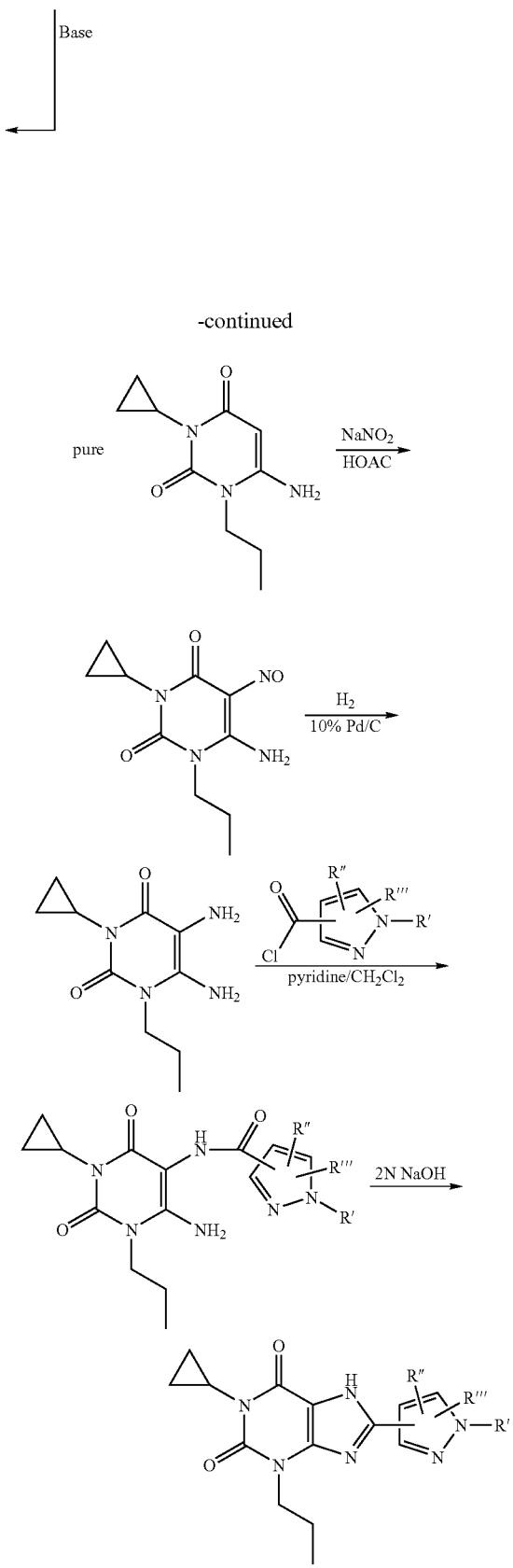

REACTION SCHEME 3
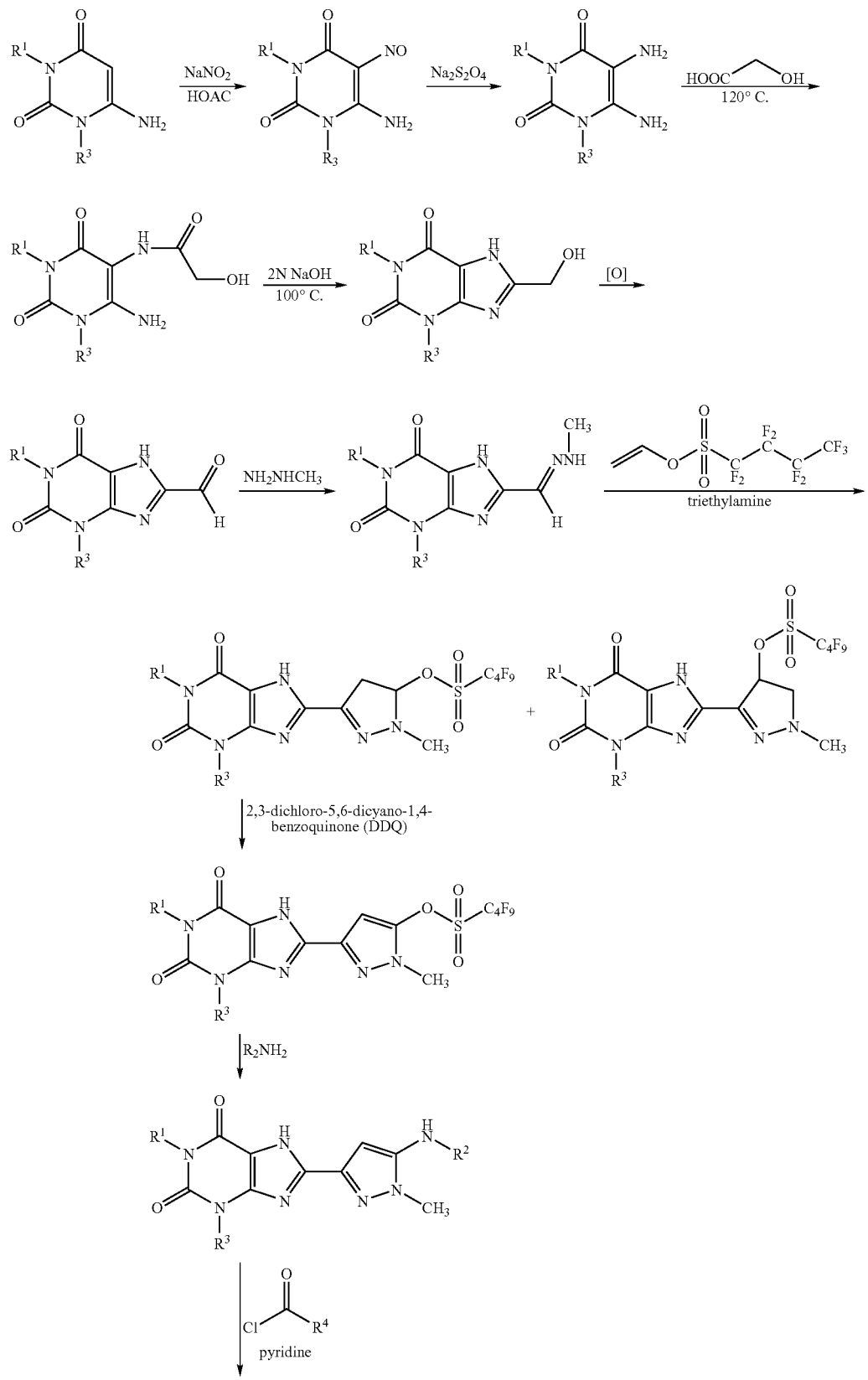

-continued

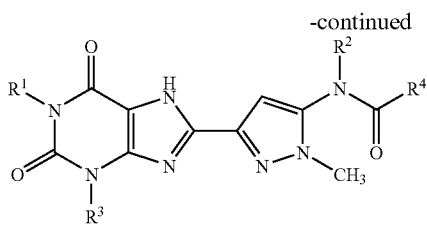

The aminouracil derivative may be prepared by contacting the substituted urea with 2-cyanoacetic acid with a dehydrating agent, such as an acid anhydride. For example, the dialkyl urea may be treated with an excess of cyanoacetic acid in acetic anhydride, and the resulting mixture may be heated above room temperature until the reaction is deemed complete. While a solvent may be added, typically, the reaction is performed without any additional solvent, and the reaction may be heated at about 50° C. to about 115° C., preferably at about 65° C. to about 100° C., more preferably at about 80° C. until the reaction is deemed complete. The acid anhydride may be removed from the reaction mixture by any methods, such as rotoevaporation or distillation under reduced pressure. The resulting residue may be dissolved in an aqueous alcoholic solvent such as methanol and 20% NaOH below room temperature, or about 0° C. to about 5° C. The resulting mixture may be stirred at the same temperature for about 1 hour and then warmed to about room temperature for about one hour. Excess solvent may be removed under reduced pressure and the resulting crude product may be isolated and purified.

In the case of the reaction of the dialkyl urea with cyanoacetic acid, the resulting product is a mixture of the aminouracil A and B, and substantially pure aminouracil A may be obtained by silica gel column chromatography or by HPLC with a C-18 column. Isolation and/or purification of the desired aminouracil isomer may also be accomplished by converting a mixture of the isomers A and B into a derivative having different physical characteristics that may be further isolated by crystallization, distillation or chromatography.

The 5-nitrosouracil derivative may be obtained by the nitrosylation of the aminouracil A or B using standard nitration reagents. Examples of such agents include, for example, $NaNO_2/AcOH$, $HNO_3/H_2SO4$, $N_2O_5/P_2O_5/CCl_4$, HONO, $EtONO_2$, $CH_3COONO_2$ and $NO_2^+CF_3SO_3^-$ that forms the nitro or the nitrosouracil derivative. Thus, the aminouracil may be dissolved in an aqueous acid, such as acetic acid and water below room temperature, such as about 10° C., and $NaNO_2$ in water is added to the aminouracil. When the reaction is deemed complete, the volatiles are removed under reduced pressure and the residue is redissolved in a mixture of solvents. Example of such mixtures of solvents include alcohols in an organic solvent, such as absolute ethanol in DCM. The resulting mixture is heated and the hot mixture may be filtered through a filter aid such as Celite 545 to remove insoluble inorganic salts. The solvent or solvent mixtures may evaporated under reduced pressure to afford the desired 5-nitrouracil or 5-nitrosouracil.

Reduction of the 5-nitrosouracil may be performed using various reagents known in the art for the reduction to nitro or nitroso compounds to the corresponding amine. Thus, the 5-nitrosouracil may be dissolved in an alcoholic solvent such as absolute ethanol, and reduced using hydrogen gas and a catalyst, such as 10% Pd/C. Once the reaction is deemed complete, the resulting mixture may be filtered through a layer of Celite 545, and the volatiles removed under reduced pressure. The resulting product, '5,6-diaminouracil may be further purified, or may used as is in the following reaction without further purification.

Acylation of the '5,6-diaminouracil may be performed using various acylating agents as known in the art, and the reaction may be conducted in an aprotic solvent. Example of such aprotic solvent may be an amine, such as pyridine that may be used to form the acid salt of the amine. Thus, the '5,6-diaminouracil may be treated with an acid halide, such as 6-chloronicotinoyl chloride in DCM and pyridine at about below room temperature, such as at about 5° C. and then warmed to about room temperature to drive the reaction to completion. Once the reaction is complete, the solvent is removed under reduced pressure to afford an oily residue. The reaction mixture may be used as is in the subsequent reaction or may be further purified and isolated if desired. An aqueous base solution, such as 2N NaOH is added to the oil, and the resulting mixture is heated under reflux until the reaction is complete and the xanthine derivative is formed. The mixture is then cooled to about room temperature, and the pH is adjust to neutral pH, or about pH of 7 with acid, such as concentrated HCl. Once a solid product is formed, the product is collected by filtration and washed with water and organic solvent or solvent mixture, such as with diethyl ether and chloroform. The product may used as is in the subsequent reaction without further purification, or if desired, the product may be further purified.

The xanthine may be further converted to the corresponding substituted amine by the reaction of the xanthine with a nucleophile, such as an amine or a protected amine, under pressure, such as a sealed tube in a solvent, such as ethanol. The resulting mixture may be degassed and sealed under an inert atmosphere such as argon. The sealed reaction mixture may be heated at an elevated temperature, such as at about 100° C. to about 200° C. or at about 160° C. for about 48 to 60 hours, or until the reaction is deemed complete. After the mixture is cooled to room temperature and a solvent such as ether is added, and the solids are filtered to obtain the desired product.

Where the acylation of the product is desired to form the acylated derivative, acylation may be performed by contacting the amine with an acyl halide such as an acyl chloride in a solvent and base, such as an amine base such as pyridine. The resulting mixture may be stirred at about room temperature for about 24 to about 60 hours until the reaction is deemed complete. Removal of the solvent under reduced pressure followed by purification, where desired, by column chromatography or crystallization, provides the desired acylated product.

In each of the above processing step, where the resulting product from the reaction is the desired product or product mixtures, optionally, the intermediate compound(s) may be used in the subsequent step without further purification. However, as noted above, the purification and isolation of compound of formula A from the compound of formula B, for example, is necessary at this particular step because the two isomers A and B cannot be readily separated in any subsequent steps. Thus, the isolation of the compound of formula A from the compound of formula B allows the preparation of the desired isomer in the subsequent processing steps.

The following abbreviations have been used herein:
[$^{125}$I]ABA [$^{125}$I]N$^6$-(4-aminobenzyl)-adenosine
$^{125}$I-ABOPX   $^{125}$I-3-(4-amino-3-iodobenzyl)-8-oxyacetate-1-propyl-xanthine
AR adenosine receptor
CGS 21680 2-[4-[(2-carboxyethyl)phenyl]ethyl-amino]-5'-N-ethylcarbamoyl adenosine
CPX 8-cyclopentyl-1,3-dipropylxanthine
DMEM Dulbecco modified eagle medium
DCM Dichloromethane
DMF N,N-dimethylformamide
DMSO dimethylsulfoxide
EDTA ethylenediaminetetraacetate
HEK cells human embryonic kidney cells
K$_i$ equilibrium inhibition constant
NECA 5'-(N-ethylcarbamoyl)adenosine
R-PIA R—N$^6$-phenylisopropyladenosine
TEA triethylamine
TLC Thin layer chromatography
ZM 241385 4-(2-[7-amino-2-{furyl}{1,2,4}triazolo{2,3-a}{1,3,5}triazin-5-ylaminoethyl)phenol In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic or stereoisomeric form or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis or by chromatographic separation using a chiral stationary phase). It is also conventional to determine A$_{2B}$ adenosine antagonist activity using the standard tests described herein or using other similar tests which are well known in the art.

The compounds of formula I can be formulated as pharmaceutical compositions and administered to a mammalian host, such as a human patient in a variety of forms adapted to the chosen route of administration, i.e., orally or parenterally, by intravenous, intramuscular, topical, inhalation or subcutaneous routes. Exemplary pharmaceutical compositions are disclosed in "*Remington: The Science and Practice of Pharmacy*", A. Gennaro, ed., 20th edition, Lippincott, Williams & Wilkins, Philadelphia, Pa.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508). Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 1.0 to about 100 mg/kg, preferably from about 10 to about 75 mg/kg of body weight per day, more preferably 5 to about 20 mg per kilogram body weight of the recipient per day.

The compound can be conveniently administered in unit dosage form; for example, tablets, caplets, etc., containing 4 to 400 mg, preferably 10 to 200 mg, most preferably, 20 to 100 mg of active ingredient per unit dosage form.

Ideally, the active ingredient should be administered to achieve peak plasma concentrations of the active compound of from about 0.02 to about 20 µM, preferably, about 0.1 to 10 µM, most preferably, about 0.5 to about 5 µM. These concentrations may be achieved, for example, by the intravenous injection of a 0.005 to 0.5% solution of the active ingredient, or orally administered as a bolus containing about 4 to 400 mg of the active ingredient.

The compounds of the invention can be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences Volumes 16 (1980) or 18 (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

All patents, patent applications, books and literature cited in the specification are hereby incorporated by reference in their entirety. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention.

The invention will now be illustrated by the following non-limiting Examples.

EXAMPLES

Pharmacology

The ability of compounds of the invention to act as an $A_{2B}$ adenosine receptor antagonists may be determined using pharmacological models which are well known to the art or using test procedures described below.

The rat $A_{2B}$ receptor cDNA was subcloned into the expression plasmid pDoubleTrouble using techniques described in Robeva, A. et al., *Biochem. Pharmacol.*, 51, 545-555 (1996). The plasmid was amplified in competent JM109 cells and plasmid DNA isolated using Wizard Megaprep columns (Promega Corporation, Madison, Wis.). $A_{2B}$ adenosine receptors were introduced into HEK-293 cells by means of Lipofectin as described in Felgner, P. L. et al., *Proc. Natl. Acad. Sci. USA*, 84, 7413-7417 (1987).

Cell Culture

Transfected HEK cells were grown under 5% $CO_2$/95% $O_2$ humidified atmosphere at a temperature of 37° C. Colonies were selected by growth of cells in 0.6 mg/mL G418. Transfected cells were maintained in DMEM supplemented with Hams F12 nutrient mixture (1/1), 10% newborn calf serum, 2 mM glutamine and containing 50 IU/mL penicillin, 50 mg/mL streptomycin, and 0.2 mg/mL Geneticin (G418, Boehringer Mannheim). Cells were cultured in 10 cm diameter round plates and subcultured when grown confluent (approximately after 72 hours).

Radioligand Binding Studies

At $A_{2B}$ receptors: Confluent monolayers of HEK-$A_{2B}$ cells were washed with PBS followed by ice cold Buffer A (10 mM HEPES, 10 mM EDTA, pH 7.4) with protease inhibitors (10 µg/mL benzamidine, 100 µM phenylmethanesulfonyl fluoride, and 2 µg/mL of each aprotinin, pepstatin and leupeptin). The cells were homogenized in a Polytron (Brinkmann) for 20 s, centrifuged at 30,000×g, and the pellets washed twice with buffer HE (10 mM HEPES, 1 mM EDTA, pH 7.4 with protease inhibitors). The final pellet was resuspended in buffer HE, supplemented with 10% sucrose and frozen in aliquots at −80° C. For binding assays membranes were thawed and diluted 5-10 fold with HE to a final protein concentration of approximately 1 mg/mL. To determine protein concentrations, membranes, and bovine serum albumin standards were dissolved in 0.2% NaOH/0.01% SDS and protein determined using fluorescamine fluorescence. Stowell, C. P. et al., *Anal. Biochem.*, 85, 572-580 (1978).

Saturation binding assays for rat $A_{2B}$ adenosine receptors were performed with [$^3$H]ZM214,385 (17 Ci/mmol, Tocris Cookson, Bristol UK) (Ji, X. et al., *Drug Design Discov.*, 16, 216-226 (1999)) or $^{125}$I-ABOPX (2200 Ci/mmol). To prepare $^{125}$I-ABOPX, 10 µL of 1 mM ABOPX in methanol/1 M NaOH (20:1) was added to 50 µL of 100 mM phosphate buffer, pH 7.3. One or 2 mCi of Na$^{125}$I was added, followed by 10 µL of 1 mg/mL chloramine-T in water. After incubation, 20 minutes at room temperature, 50 µL of 10 mg/mL Na-metabisulfite in water was added to quench the reaction. The reaction mixture was applied to a C18 HPLC column, eluting with a mixture of methanol and 5 mM phosphate, pH 6.0. After 5 min at 35% methanol, the methanol concentration was ramped to 100% over 15 min. Unreacted ABOPX eluted in 11-12 minutes; $^{125}$I-ABOPX eluted at 18-19 min in a yield of 50-60% with respect to the initial $^{125}$I.

In equilibrium binding assays the ratio of $^{127}$I/$^{125}$I-ABOPX was 10-20/1. Radioligand binding experiments were performed in triplicate with 20-25 µg membrane protein in a total volume of 0.1 mL HE buffer supplemented with 1 U/mL adenosine deaminase and 5 mM MgCl$_2$. The incubation time was 3 h at 21° C. Nonspecific binding was measured in the presence of 100 µM NECA. Competition experiments were carried out using 0.6 nM $^{125}$I-ABOPX. Membranes were filtered on Whatman GF/C filters using a Brandel cell harvester (Gaithersburg, Md.) and washed 3 times over 15-20 seconds with ice cold buffer (10 mM Tris, 1 mM MgCl$_2$, pH 7.4). B$_{max}$ and K$_D$ values were calculated by Marquardt's nonlinear least squares interpolation for single a site binding models. Marquardt, D. M., *J. Soc. Indust. Appl. Math.*, 11, 431-441.21 (1963). K$_i$ values for different compounds were derived from IC$_{50}$ values as described. Linden, J., *J. Cycl. Nucl. Res.*, 8, 163-172 (1982). Data from replicate experiments are tabulated as means±SEM.

At other Adenosine Receptors: [$^3$H]CPX. Bruns, R. F. et al., *Naunyn-Schmiedeberg's Arch. Pharmacol.*, 335, 59-63 (1987). $^{125}$I-ZM241385 and $^{125}$I-ABA were utilized in radioligand binding assays to membranes derived from HEK-293 cells expressing recombinant rat A$_1$, A$_{2A}$ and A$_3$ ARs, respectively. Binding of [$^3$H]R—N-6-phenylisopropyladenosine. Schwabe, U. et al., *Naunyn-Schmiedeberg's Arch. Pharmacol.*, 313, 179-187 (1980). ([$^3$H]R-PIA, Amersham, Chicago, Ill.) to A$_1$ receptors from rat cerebral cortical membranes and of [$^3$H]CGS 21680. Jarvis, M. F. et al., *J. Pharmacol. Exp. Therap.*, 251, 888-893 (1989). (Dupont NEN, Boston, Mass.) to $A_{2A}$ receptors from rat striatal membranes was performed as described. Adenosine deaminase (3 units/mL) was present during the preparation of the brain membranes, in a pre-incubation of 30 min at 30° C., and during the incubation with the radioligands. All non-radioactive compounds were initially dissolved in DMSO, and diluted with buffer to the final concentration, where the amount of DMSO never exceeded 2%. Incubations were terminated by rapid filtration over Whatman GF/B filters, using a Brandell cell harvester (Brandell, Gaithersburg, Md.). The tubes were rinsed three times with 3 mL buffer each.

At least six different concentrations of competitor, spanning 3 orders of magnitude adjusted appropriately for the IC$_{50}$ of each compound, were used. IC$_{50}$ values, calculated with the nonlinear regression method implemented in (Graph-Pad Prism, San Diego, Calif.), were converted to apparent K$_i$ values as described. Linden, J., *J. Cycl. Nucl. Res.*, 8:163-172 (1982). Hill coefficients of the tested compounds were in the range of 0.8 to 1.1.

Functional Assay

HEK-$A_{2B}$ cells from one confluent T75 flask were rinsed with Ca$^{2+}$ and Mg$^{2+}$-free Dulbecco's phosphate buffered saline (PBS) and then incubated in Ca$^{2+}$ and Mg$^{2+}$-free HBSS with 0.05% trypsin and 0.53 mM EDTA until the cells detached. The cells were rinsed twice by centrifugation at 250×g in PBS and resuspended in 10 mL of HBSS composed of 137 mM NaCl, 5 mM KCl, 0.9 mM MgSO$_4$, 1.4 mM CaCl$_2$, 3 mM NaHCO$_3$, 0.6 mM Na$_2$HPO$_4$, 0.4 mM KH$_3$PO$_4$, 5.6 mM glucose, and 10 mM HEPES, pH 7.4 and the Ca$^{2+}$-sensitive fluorescent dye indo-1-AM (5 µM) 37° C. for 60 min. The cells were rinsed once and resuspended in 25 mL dye-free HBSS supplemented with 1 U/ml adenosine deaminase and held at room temperature. Adenosine receptor antagonists prepared as 100× stocks in DMSO or vehicle was added and the cells and transferred to a 37° C. bath for 2 minutes. Then the cells (1 million in 2 ml) were transferred to a stirred cuvette maintained at 37° C. within an Aminco SLM 8000 spectrofluorometer (SML instruments, Urbana Ill.). The ratios of indo-1 fluorescence obtained at 400 and 485 nm (excitation, 332 nm) was recorded using a slit width of 4 nm. NECA was added after a 100 s equilibration period.

Cyclic AMP Accumulation

Cyclic AMP generation was performed in DMEM/HEPES buffer (DMEM containing 50 mM HEPES, pH 7.4, 37° C.). Each well of cells was washed twice with DMEM/HEPES buffer, and then 100 µL adenosine deaminase (final concentration 10 IU/mL) and 100 µL of solutions of rolipram and cilostamide (each at a final concentration of 10 µM) were added, followed by 50 µL of the test compound (appropriate concentration) or buffer. After 15 minutes, incubation at 37° C. was terminated by removing the medium and adding 200 µL of 0.1 M HCl. Acid extracts were stored at −20° C. until assay. The amounts of cyclic AMP were determined following a protocol which utilized a cAMP binding protein (PKA) [van der Wenden et al., 1995], with the following minor modifications. The assay buffer consisted of 150 mM K$_2$HPO$_4$/10 mM EDTA/0.2% BSA FV at pH 7.5. Samples (20 mL) were incubated for 90 minutes at 0° C. Incubates were filtered over GF/C glass microfiber filters in a Brandel M-24 Cell Harvester. The filters were additionally rinsed with 4 times 2 mL 150 mM K$_2$HPO$_4$/10 mM EDTA (pH 7.5, 4° C.). Punched filters were counted in Packard Emulsifier Safe scintillation fluid after 2 hours of extraction.

Available data from the affinity testing for the compounds of the invention are reported in Table 1. The data reported for the $A_{2B}$ term is the level of displacement of specific [$^{125}$I] ABOPX binding at rat $A_{2B}$ receptors (r$A_{2B}$) expressed in HEK-293 cells.

Synthesis and Characterization

Proton nuclear magnetic resonance spectroscopy was performed on a Varian-300 MHz spectrometer and spectra were taken in DMSO-$d_6$ or CDCl$_3$. Unless noted, chemical shifts are expressed as ppm downfield from tetramethylsilane or relative ppm from DMSO (2.5 ppm). Electro-spray-ionization (ESI) mass spectrometry was performed with a ThermoFinnigan LCQ mass spectrometer.

All xanthine derivatives were homogeneous as judged using TLC (Silica gel 60 $F_{254}$, 0.25 mm, aluminium backed, EM Science, Gibbstown, N.J.) and HPLC (Shimadzu) using Varian C18 5 micron analytical column (4.6 mm×150 mm) in linear gradient or isocratic solvent system, at a flow rate of 1 ml/min. The solvent system used was MeOH (0.1% formic acid): H$_2$O (0.1% formic acid). Peaks were detected by UV absorption at 232 nm and 254 nm. NMR and mass spectra were shown to be consistent with the assigned structure.

The general procedures for the preparation of xanthine derivatives of the present invention are described herein above. The following compounds of the invention are prepared using the procedures described:

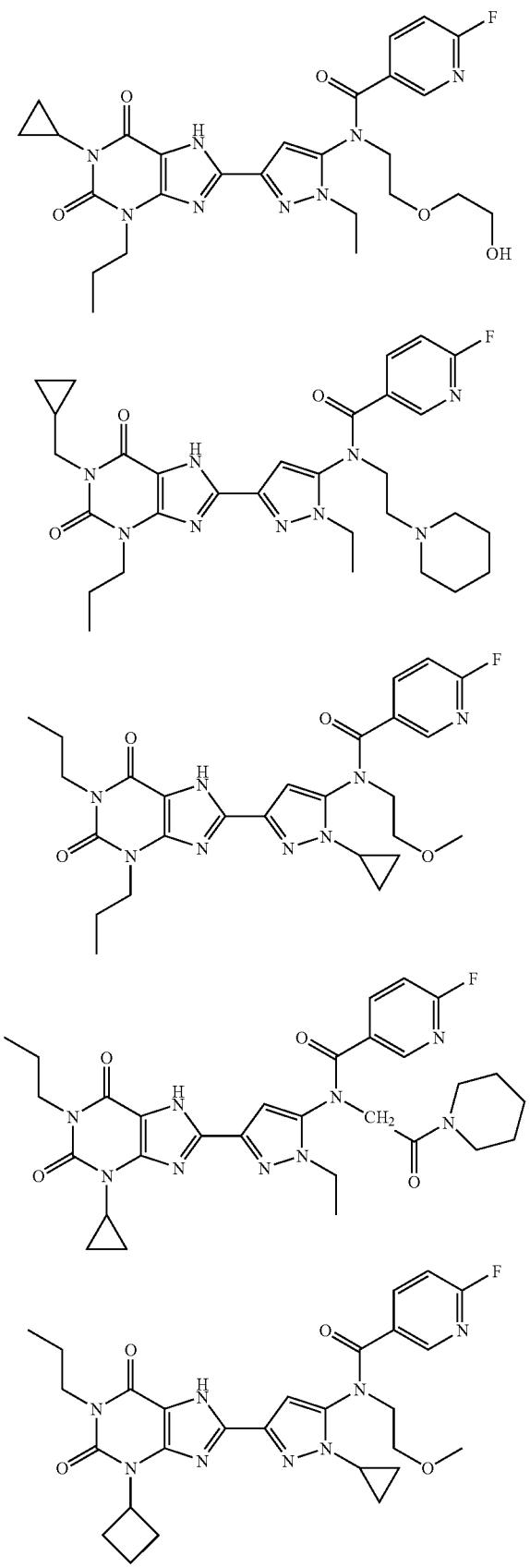

-continued
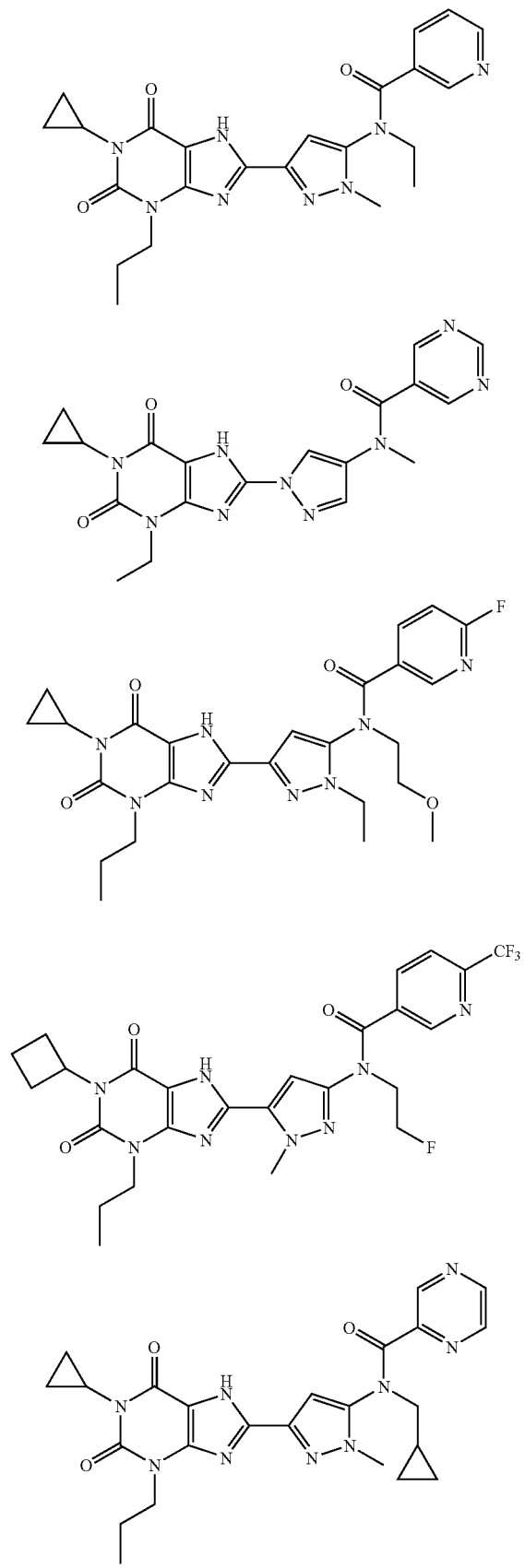
-continued
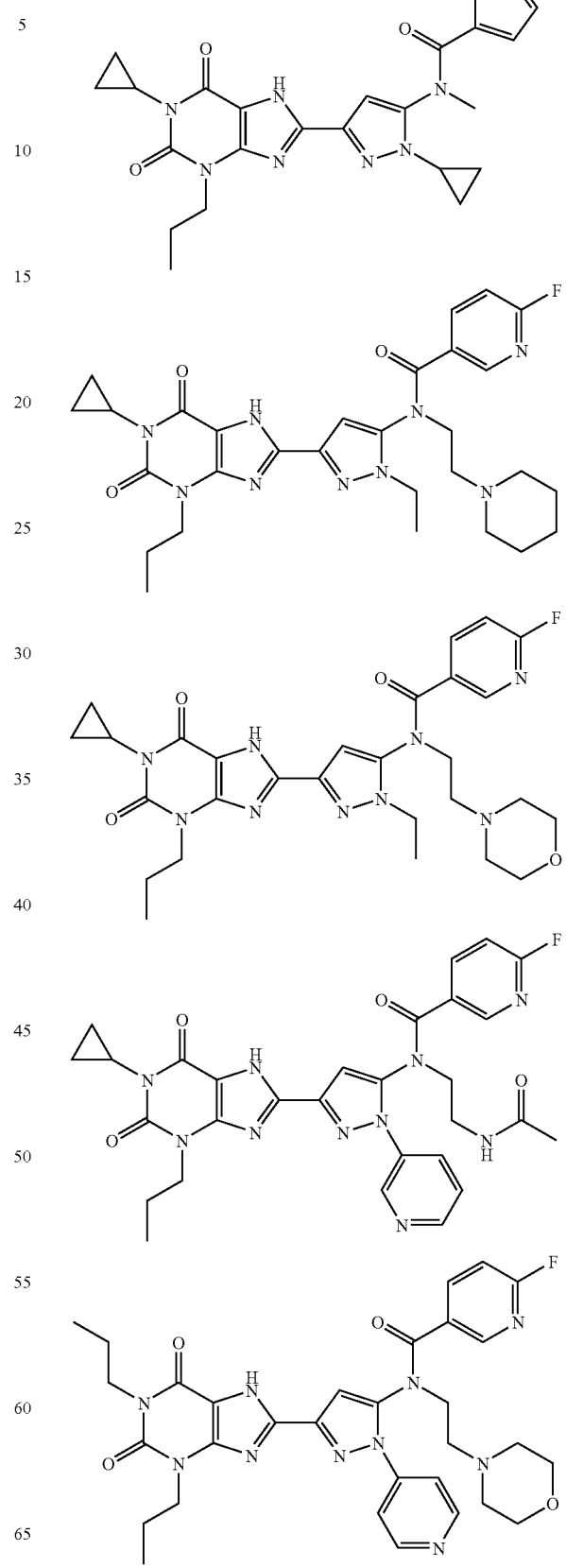

-continued

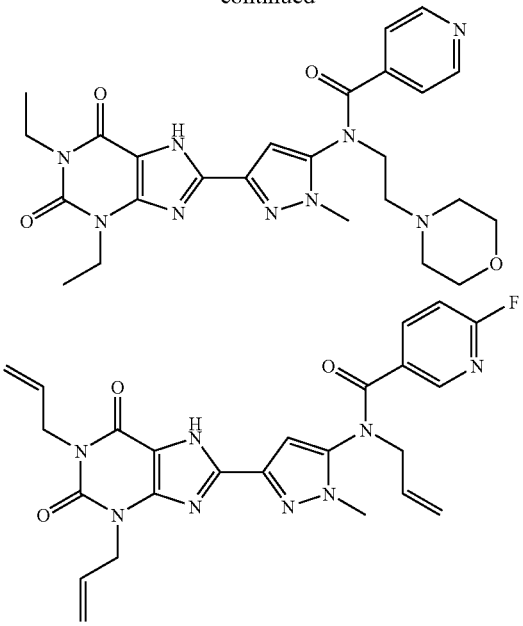

What is claimed is:
1. A compound of formula I:

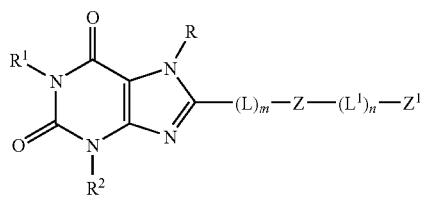

wherein:
R is hydrogen or is selected from the group consisting of $(C_{1-5})$alkyl, halo$(C_{1-8})$alkyl, $(C_{3-8})$cycloalkyl, $(C_{3-8})$cycloalkyl$(C_{1-8})$alkyl-, $(C_{3-5})$alkenyl and $(C_{3-5})$alkynyl, each substituted or unsubstituted;
one of $R^1$ and $R^2$ is selected from the group consisting of cyclopropyl, cyclopropylmethyl, cyclobutyl, hydroxycyclobutyl, trihalomethylcyclobutyl and cyclopentyl;
the other of $R^1$ and $R^2$ is selected from the group consisting of hydrogen, substituted or unsubstituted $(C_{1-8})$alkyl, halo$(C_{1-8})$alkyl, $(C_{3-8})$alkenyl, $(C_{3-8})$alkenyl$(C_{1-8})$alkyl, $(C_{3-8})$alkynyl, $(C_{3-8})$alkynyl$(C_{1-8})$alkyl, $(C_{1-8})$alkoxy, $(C_{3-8})$cycloalkyl, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryloxy, $(C_{6-10})$aryl$(C_{1-8})$alkyl-, $(C_{5-10})$heteroaryl and $(C_{5-10})$heteroaryl$(C_{1-8})$alkyl-;
L and $L^1$ are each independently a linker selected from the group consisting of substituted or unsubstituted —NR$^o$—C(O)—, —NCH$_3$—C(O)—, —NR$^o$—S(O)—, —NCH$_3$—S(O)—, —NR$^o$—S(O)$_2$—, —NCH$_3$—S(O)$_2$—, —C(O)NR$^o$—, —C(O)NCH$_3$—, —NR$^o$C(O)CH$_2$—, —NR$^o$C(O)CH$_2$CH$_2$—, —C(O)NR$^o$CH$_2$—, —C(O)NR$^o$CH$_2$CH$_2$—, —C(O)CH$_2$NR$^o$—, —C(O)CH$_2$CH$_2$NR$^o$—, —CH$_2$NR$^o$C(O)—, —CH$_2$CH$_2$NR$^o$C(O)—, —CH$_2$C(O)NR$^o$—, —CH$_2$CH$_2$C(O)NR$^o$—, —NR$^o$CH$^2$C(O)— and —NR$^o$CH$_2$CH$_2$C(O)—, wherein each R$^o$ is independently hydrogen or substituted or unsubstituted $(C_{1-4})$alkyl, $(C_{1-4})$alkylC(O)—, $(C_{6-10})$arylC(O)— and $(C_{5-10})$heteroarylC(O)—,
Z is a substituted or unsubstituted heteroaryl ring selected from the group consisting of imidazolyl, triazolyl, pyrrolyl, pyrazolyl and tetrazolyl;
$Z^1$ is a 5-14 member substituted or unsubstituted heteroaryl ring;
where m is 0, 1 or 2;
n is 1 or 2; or
a pharmaceutically acceptable salt thereof.

2. The compound of claim 1, wherein L and $L^1$ are each independently unsubstituted or further substituted by a substituent selected from the group consisting of $(C_{1-4})$alkoxy, $(C_{1-8})$alkylamino, $(C_{3-8})$cycloalkyl, $(C_{3-8})$cycloalkyl$(C_{1-8})$alkyl-, $(C_{1-4})$alkoxy$(C_{1-4})$alkyl, halo, hydroxy, cyano, nitro, $(C_{1-8})$alkyl, $(C_{6-10})$aryl, —O$(C_{6-10})$aryl, hydroxy$(C_{1-8})$alkyl, R$^b$R$^c$N$(C_{1-8})$alkyl, halo$(C_{1-8})$alkyl, —NR$^b$R$^c$, $(C_{1-8})$alkyl)C(O)—, $(C_{1-8})$alkylCO$_2$—, —C(O)N$((C_{1-8})$alkyl)$_2$, —S(O)$(C_{1-8})$alkyl, —S(O)N$((C_{1-8})$alkyl)$_2$, —S(O)$_2(C_{1-8})$alkyl, —S(O)$_2$N$((C_{1-8})$alkyl)$_2$, —S(O)$_{1-3}$—NR$^4$R$^5$, —NR$^4$R$^5$, $(C_{4-10})$heterocyclyl$(C_{1-8})$alkyl-, or $(C_{4-10})$heterocyclyl wherein the heterocyclyl is optionally substituted with 1, 2, 3 or 4 substituents independently selected from halo, hydroxy, cyano, nitro, —OR$^a$, —SR$^a$, $(C_{1-8})$alkyl, $(C_{6-10})$aryl, —O$(C_{6-10})$aryl, hydroxy$(C_{1-8})$alkyl, R$^b$R$^c$N$(C_{1-8})$alkyl, halo$(C_{1-8})$alkyl, —NR$^b$R$^c$, $(C_{1-8})$alkyl)C(O)—, $(C_{1-8})$alkylCO$_2$—, —C(O)N$((C_{1-8})$alkyl)$_2$, —S(O)$(C_{1-8})$alkyl, —S(O)N$((C_{1-8})$alkyl)$_2$, —S(O)$_2(C_{1-8})$alkyl, —S(O)$_2$N$((C_{1-8})$alkyl)$_2$, —C(O)R$^b$, —COOR$^b$, and —C(O)NR$^b$R$^c$; wherein R$^a$ is hydrogen, or $(C_{1-6})$alkyl; R$^b$ and R$^c$ are each independently hydrogen, $(C_{1-6})$alkyl, $(C_{1-6})$alkoxy, $(C_{3-8})$cycloalkyl, $(C_{1-6})$alkylthio, $(C_{6-10})$aryl, $(C_{1-6})$aryl$(C_{1-6})$alkyl-, heteroaryl, or heteroaryl$(C_{1-6})$alkyl-; or R$^b$ and R$^c$ together with the nitrogen to which they are attached, form a pyrrolidyl, piperidyl, piperazinyl, azepinyl, diazepinyl, morpholinyl or thiomorpholinyl ring; and wherein R$^4$ and R$^5$ each are each independently hydrogen or are selected from the group consisting of $(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkyl$(C_{1-8})$alkyl-, $(C_{6-18})$polycycloalkyl, $(C_{6-18})$polycycloalkyl$(C_{1-8})$alkyl-, $(C_{3-10})$heterocyclyl, $(C_{3-10})$heterocyclyl$(C_{1-8})$alkyl-, $((C_{1-8})$alkyl)$_2$ N— $(C_{6-10})$aryl, $(C_{6-10})$aryl$(C_{1-8})$alkyl-, $(C_{5-10})$heteroaryl, $(C_{5-10})$alkyl)$_2$, —S(O)$(C_{1-8})$alkyl, —S(O)N$((C_{1-8})$alkyl)$_2$, —S(O)$_2(C_{1-8})$alkyl or —S(O)$_2$N$((C_{1-8})$alkyl)$_2$.

3. The compound of claim 1, wherein the compound is selected from a compound of any one of formulae IIa to IIm:

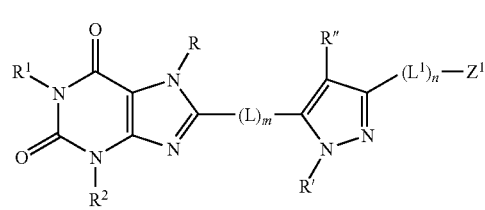
IIa

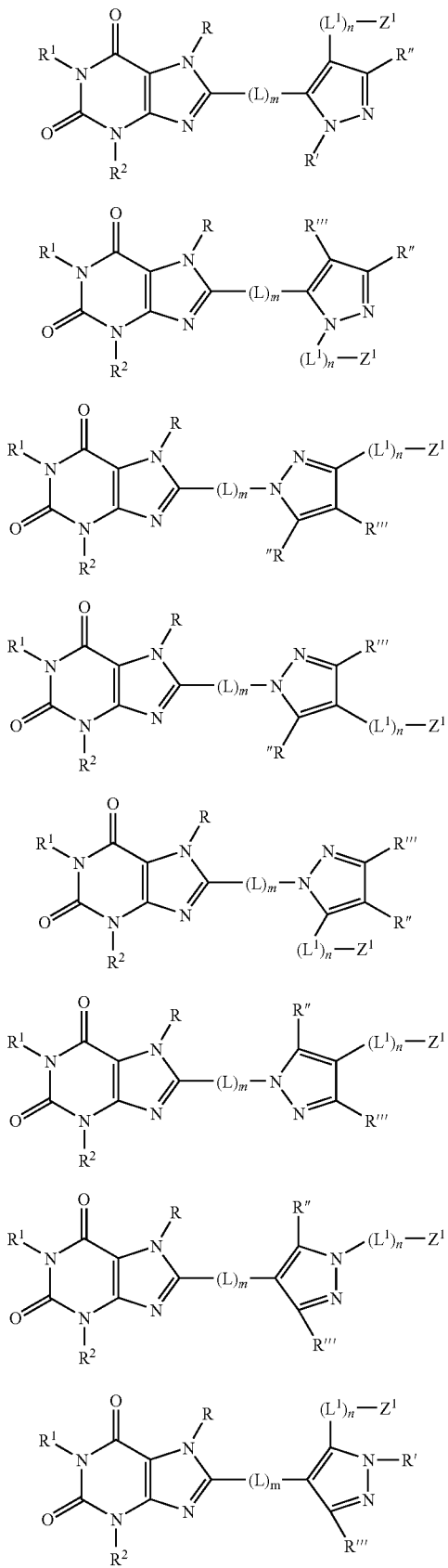
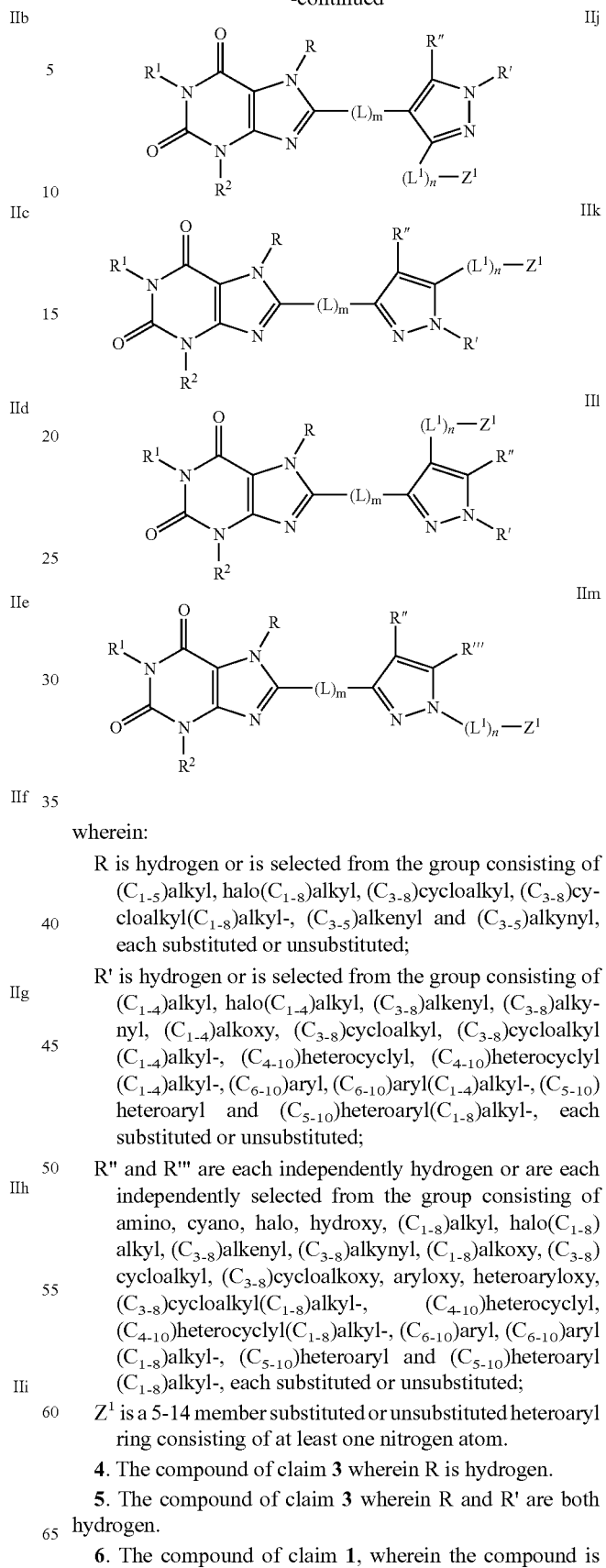

wherein:

R is hydrogen or is selected from the group consisting of $(C_{1-5})$alkyl, halo$(C_{1-8})$alkyl, $(C_{3-8})$cycloalkyl, $(C_{3-8})$cycloalkyl$(C_{1-8})$alkyl-, $(C_{3-5})$alkenyl and $(C_{3-5})$alkynyl, each substituted or unsubstituted;

R' is hydrogen or is selected from the group consisting of $(C_{1-4})$alkyl, halo$(C_{1-4})$alkyl, $(C_{3-8})$alkenyl, $(C_{3-8})$alkynyl, $(C_{1-4})$alkoxy, $(C_{3-8})$cycloalkyl, $(C_{3-8})$cycloalkyl $(C_{1-4})$alkyl-, $(C_{4-10})$heterocyclyl, $(C_{4-10})$heterocyclyl $(C_{1-4})$alkyl-, $(C_{6-10})$aryl, $(C_{6-10})$aryl$(C_{1-4})$alkyl-, $(C_{5-10})$heteroaryl and $(C_{5-10})$heteroaryl$(C_{1-8})$alkyl-, each substituted or unsubstituted;

R" and R''' are each independently hydrogen or are each independently selected from the group consisting of amino, cyano, halo, hydroxy, $(C_{1-8})$alkyl, halo$(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkoxy, aryloxy, heteroaryloxy, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryl $(C_{1-8})$alkyl-, $(C_{5-10})$heteroaryl and $(C_{5-10})$heteroaryl $(C_{1-8})$alkyl-, each substituted or unsubstituted;

$Z^1$ is a 5-14 member substituted or unsubstituted heteroaryl ring consisting of at least one nitrogen atom.

4. The compound of claim 3 wherein R is hydrogen.

5. The compound of claim 3 wherein R and R' are both hydrogen.

6. The compound of claim 1, wherein the compound is selected from a compound of formula IIIa or formula IIIb:

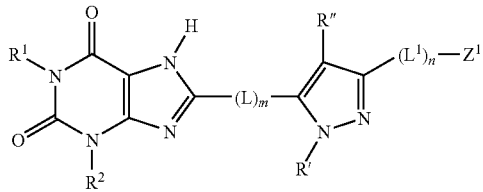

IIIa

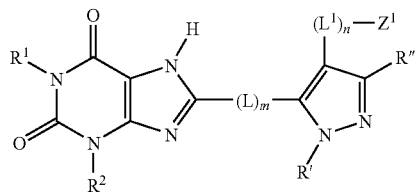

IIIb

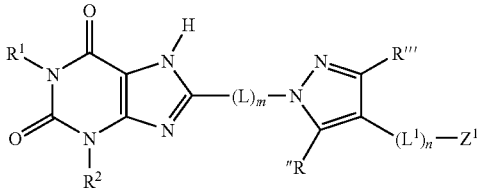

IVb

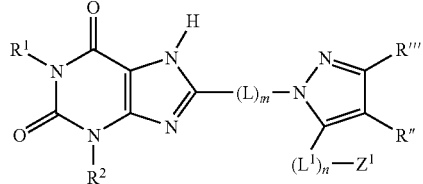

IVc wherein:

R' is hydrogen or is selected from the group consisting of (C$_{1-4}$)alkyl, halo(C$_{1-4}$)alkyl, (C$_{3-8}$)alkenyl, (C$_{3-8}$)alkynyl, (C$_{1-4}$)alkoxy, (C$_{3-8}$)cycloalkyl, (C$_{3-8}$)cycloalkyl(C$_{1-4}$)alkyl-, (C$_{4-10}$)heterocyclyl, (C$_{4-10}$)heterocyclyl(C$_{1-4}$)alkyl-, (C$_{6-10}$)aryl, (C$_{6-10}$)aryl(C$_{1-4}$)alkyl-, (C$_{5-10}$)heteroaryl and (C$_{5-10}$)heteroaryl(C$_{1-8}$)alkyl-, each substituted or unsubstituted;

R" is hydrogen or is selected from the group consisting of amino, cyano, halo, hydroxy, (C$_{1-8}$)alkyl, halo(C$_{1-8}$)alkyl, (C$_{3-8}$)alkenyl, (C$_{3-8}$)alkynyl, (C$_{1-8}$)alkoxy, (C$_{3-8}$)cycloalkyl, (C$_{3-8}$)cycloalkoxy, aryloxy, heteroaryloxy, (C$_{3-8}$)cycloalkyl(C$_{1-8}$))alkyl-, (C$_{4-10}$)heterocyclyl, (C$_{4-10}$)heterocyclyl(C$_{1-8}$)alkyl-, (C$_{6-10}$)aryl, (C$_{6-10}$)aryl(C$_{1-8}$)alkyl-, (C$_{5-10}$)heteroaryl and (C$_{5-10}$)heteroaryl(C$_{1-8}$)alkyl-, each substituted or unsubstituted;

Z$^1$ is a 5-14 member substituted or unsubstituted heteroaryl ring consisting of at least one nitrogen atom.

7. The compound according to claim 3, wherein R' is selected from the group consisting of (C$_{1-4}$)alkyl, halo(C$_{1-4}$)alkyl, hydroxy(C$_{1-4}$)alkyl, (C$_{1-4}$)alkoxy(C$_{1-4}$)alkyl, (C$_{3-8}$)alkenyl, (C$_{3-8}$)alkynyl and (C$_{1-4}$)alkoxy, each further substituted or unsubstituted.

8. The compound according to claim 3, wherein R' is hydrogen.

9. The compound according to claim 3, wherein R" is hydrogen.

10. The compound according to claim 3, wherein R' and R" are both hydrogen.

11. The compound of claim 1, wherein the compound is selected from a compound of the formula IVa, IVb or IVc:

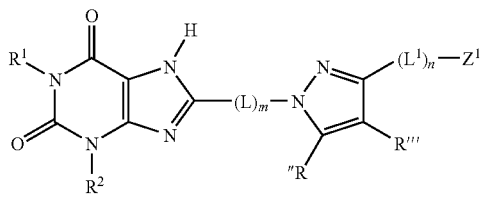

IVa wherein:

R" and R'" are each independently hydrogen or are each independently selected from the group consisting of amino, cyano, halo, hydroxy, (C$_{1-8}$)alkyl, halo(C$_{1-8}$)alkyl, (C$_{3-8}$)alkenyl, (C$_{3-8}$)alkynyl, (C$_{1-8}$)alkoxy, (C$_{3-8}$)cycloalkyl, (C$_{3-8}$)cycloalkoxy, aryloxy, heteroaryloxy, (C$_{3-8}$)cycloalkyl(C$_{1-8}$)alkyl-, (C$_{4-10}$)heterocyclyl, (C$_{4-10}$)heterocyclyl(C$_{1-8}$)alkyl-, (C$_{6-10}$)aryl, (C$_{6-10}$)aryl (C$_{1-8}$)alkyl-, (C$_{5-10}$)heteroaryl and (C$_{5-10}$)heteroaryl (C$_{1-8}$)alkyl-, each substituted or unsubstituted;

Z$^1$ is a 5-14 member substituted or unsubstituted heteroaryl ring consisting of at least one nitrogen atom.

12. The compound according to claim 3, wherein R" and R'" are each independently hydrogen or are each selected from the group consisting of amino, cyano, halo, hydroxy, (C$_{1-8}$)alkyl, halo(C$_{1-8}$)alkyl, (C$_{3-8}$)alkenyl, (C$_{3-8}$)alkynyl, (C$_{1-8}$)alkoxy, (C$_{3-8}$)cycloalkyl, (C$_{3-8}$)cycloalkoxy, aryloxy, heteroaryloxy, (C$_{3-8}$)cycloalkyl(C$_{1-8}$)alkyl-, (C$_{4-10}$)heterocyclyl, (C$_{4-10}$)heterocyclyl(C$_{1-8}$)alkyl-, (C$_{6-10}$)aryl, (C$_{6-10}$)aryl (C$_{1-8}$)alkyl-, (C$_{5-10}$)heteroaryl and (C$_{5-10}$)heteroaryl(C$_{1-8}$) alkyl-, each substituted or unsubstituted.

13. The compound according to claim 3, wherein R" and R'" are each independently selected from the group consisting of (C$_{1-4}$)alkyl, (C$_{3-4}$)alkenyl, (C$_{3-4}$)alkynyl, phenyl, phenyl (C$_{1-4}$)alkyl, (C$_{3-6}$)cycloalkyl and (C$_{3-6}$)cycloalkyl(C$_{1-4}$) alkyl-.

14. The compound according to claim 3, wherein R" and R'" are each hydrogen or are each independently selected from the group consisting of methyl, ethyl, allyl, propargyl, i-propyl, n-propyl, n-butyl, i-butyl, phenyl, phenethyl, benzyl, (methoxyphenyl)ethyl, (C$_{3-6}$)cycloalkyl and (C$_{3-6}$)cycloalkyl(C$_{1-4}$)alkyl-.

15. The compound according to claim 3, wherein R" and R'" are each hydrogen or are each independently selected from the group consisting of amino, cyano, halo, hydroxy, (C$_{1-8}$)alkyl, halo(C$_{1-8}$)alkyl and (C$_{3-8}$)alkenyl.

16. The compound according to claim 1, wherein Z$^1$ is a substituted or unsubstituted heteroaryl ring selected from the group consisting of benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, pteridine, purine, carbazole, acridine, imidazolyl, triazolyl, triazinyl, oxazoyl, isoxazoyl, thiazolyl, isothiazoyl, thiodiazolyl, thiophenyl, pyrrolyl, pyrazolyl, pyrazinyl, tetrazolyl, pyridinyl, pyrimidinyl, indolyl, isoquinolyl and quinolyl.

17. The compound of claim 16, wherein $Z^1$ is a substituted or unsubstituted heteroaryl ring selected from the group consisting of imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, imidazo[1,5-a]pyridine, pyrazolo[1,5-a]pyridine, pteridine, purine, pyridinyl and pyrimidinyl.

18. The compound of claim 16, wherein $Z^1$ is a substituted or unsubstituted heteroaryl ring selected from the group consisting of benzo[b]furan, benzo[b]thiophene, benzimidazole, indole, isoindole, indazole, indoline, benzoxazole, benzopyrazole, benzothiazole, carbazole, acridine, imidazolyl, triazolyl, triazinyl, oxazoyl, isoxazoyl, thiazolyl, isothiazoyl, thiodiazolyl, pyrrolyl, pyrazolyl, pyrazinyl, tetrazolyl, indolyl, isoquinolyl and quinolyl.

19. The compound of claim 16 wherein $Z^1$ is substituted by 1, 2 or 3 substituents independently selected from the group consisting of $(C_{1-8})$alkyl, $(C_{2-8})$alkenyl, $(C_{2-8})$alkynyl, —$OR^6$, —$SR^6$, cyano, nitro, halo, hydroxy, $R^6O(C_{1-8})$alkyl, $R^7R^8N(C_{1-8})$alkyl, halo$(C_{1-8})$alkyl, —$NC(O)R^6$, —$NR^7R^8$, $R^7R^8N(C_{1-8})$alkyl, —$C(O)R^6$, —$COOR^6$ and —$C(O)NR^7R^8$; wherein
- $R^6$ is hydrogen, $(C_{1-8})$ alkyl, $R^bO(C_{1-8})$alkyl, $R^bR^cN(C_{1-8})$alkyl, halo$(C_{1-8})$alkyl, $(C_{3-10})$heterocyclyl, $(C_{3-10})$heterocyclyl$(C_{1-8})$alkyl-, $(C_{6-10})$aryl, $(C_{6-10})$aryl$(C_{1-8})$alkyl-, $(C_{4-10})$heteroaryl or $(C_{4-10})$heteroaryl$(C_{1-8})$alkyl-; wherein the heterocyclyl, heteroaryl or aryl are optionally substituted with 1, 2, 3 or 4 substituents independently selected from halo, hydroxy, cyano, nitro, —$OR^a$, —$SR^a$, $(C^{6-10})$aryl, —$O(C^{6-10})$aryl, hydroxy$(C_{1-8})$alkyl, $R^bR^cN(C_{1-8})$alkyl, halo$(C_{1-8})$alkyl, halo$(C_{1-8})$alkyl, —$NR^bR^c$, —$C(O)R^b$, —$COOR^b$ and —$C(O)NR^bR^c$;
- $R^7$ and $R^8$ are each independently hydrogen, $(C_{1-8})$alkyl, $R^bO(C_{1-8})$alkyl, $R^bR^cN(C_{1-8})$alkyl, halo$(C_{1-8})$alkyl, $(C_{3-10})$heterocyclyl, $(C_{6-10})$aryl, $(C_{6-10})$aryl$(C_{1-8})$alkyl-, $(C_{4-10})$heteroaryl; —$COOR^b$, —$C(O)R^b$ or —$C(O)NR^bR^c$ wherein the heterocyclyl, heteroaryl or aryl are optionally substituted with 1, 2, 3 or 4 substituents independently selected from halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COOR^b$ and —$C(O)NR^bR^c$; or $R^7$ and $R^8$ together with the atoms to which they are attached form a saturated or partially unsaturated, mono-, bicyclic- or aromatic ring having 3, 4, 5, 6, 7 or 8, ring atoms optionally ring having from 4 to eight ring atoms and optionally consisting of 1, 2, 3 or 4 heteroatoms selected from non-peroxide oxy, —S—, sulfinyl, sulfonyl or —NH— in the ring;
- $R^a$ is hydrogen, or $(C_{1-6})$alkyl; $R^b$ and $R^c$ are each independently hydrogen, $(C_{1-6})$alkyl, $(C_{1-6})$alkoxy, $(C_{3-8})$cycloalkyl, $(C_{1-6})$alkylthio, $(C_{6-10})$aryl, $(C_{6-10})$aryl$(C_{1-6})$alkyl-, heteroaryl or heteroaryl$(C_{1-6})$alkyl-; or $R^b$ and $R^c$ together with the nitrogen to which they are attached, form a pyrrolidyl, piperidyl, piperazinyl, azepinyl, diazepinyl, morpholinyl or thiomorpholinyl ring.

20. The compound of claim 16 wherein $Z^1$ is substituted by 1, 2 or 3 substituents independently selected from the group consisting of amino, carbonyl, cyano, halo, hydroxy, mercapto, $(C_{1-8})$alkyl, halo$(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkoxy, aryloxy, heteroaryloxy, $(C_{3-8})$cycloalkyl$(C_{1-8})$alkyl-, $(C_{4-10})$heterocyclyl, $(C_{4-10})$heterocyclyl$(C_{1-8})$alkyl-, $(C_{6-10})$aryl, $(C_{6-10})$aryl$(C_{1-8})$alkyl-, $(C_{5-10})$heteroaryl and $(C_{5-10})$heteroaryl$(C_{1-8})$alkyl-, each substituted or unsubstituted.

21. The compound of claim 16 wherein $Z^1$ is substituted by 1, 2 or 3 substituents independently selected from the group consisting of $(C_{1-4})$alkyl, $(C_{3-4})$alkenyl, $(C_{3-4})$alkynyl, phenyl, phenyl$(C_{1-4})$alkyl, $(C_{3-6})$cycloalkyl and $(C_{3-6})$cycloalkyl$(C_{1-4})$alkyl-.

22. The compound of claim 16 wherein $Z^1$ is substituted by 1, 2 or 3 substituents independently selected from the group consisting of methyl, ethyl, allyl, propargyl, i-propyl, n-propyl, n-butyl, i-butyl, phenyl, phenethyl, benzyl, (methoxyphenyl)ethyl, $(C_{3-6})$cycloalkyl and $(C_{3-6})$cycloalkyl$(C_{1-4})$alkyl-.

23. The compound of claim 16 wherein $Z^1$ is substituted by 1, 2 or 3 substituents independently selected from the group consisting of —$OR^3$, —$SR^3$, halo, hydroxy, —$S(O)_{1-3}$—$NR^4R^5$, —$NR^4R^5$, —$NC(O)R^6$ or $(C_{4-10})$heterocyclyl wherein the heterocyclyl is optionally substituted with 1, 2, 3 or 4 substituents independently selected from halo, cyano, nitro, —$OR^a$, —$SR^a$, $(C_{1-8})$alkyl, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COOR^b$ and —$C(O)NR^bR^c$; wherein $R^a$ is hydrogen, or $(C_{1-6})$alkyl; $R^b$ and $R^c$ are each independently hydrogen, $(C_{1-6})$alkyl, $(C_{1-6})$alkoxy, $(C_{3-8})$cycloalkyl, $(C_{1-6})$alkylthio, $(C_{6-10})$aryl, $(C_{6-10})$aryl$(C_{1-6})$alkyl-, heteroaryl or heteroaryl$(C_{1-6})$alkyl-; or $R^b$ and $R^c$ together with the nitrogen to which they are attached, form a pyrrolidyl, piperidyl, piperazinyl, azepinyl, diazepinyl, morpholinyl or thiomorpholinyl ring;
- $R^3$ is $(C_{1-8})$alkyl, $(C_{3-8})$alkenyl, $(C_{3-8})$alkynyl, $(C_{6-10})$aryl, $(C_{6-10})$aryl$(C_{1-8})$alkyl-, $(C_{5-10})$heteroaryl, $(C_{5-10})$heteroaryl$(C_{1-8})$alkyl-, —$C(O)R^6$ or —$C(O)NR^7R^8$;
- $R^4$ and $R^5$ are independently hydrogen, $(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkyl$(C_{1-8})$alkyl-, $(C_{6-18})$polycycloalkyl, $(C_{6-8})$polycycloalkyl$(C_{1-8})$alkyl-, $(C_{3-10})$heterocyclyl, $(C_{3-10})$heterocyclyl$(C_{1-8})$alkyl-, —$NR^7R^8$, $(C_{6-10})$aryl, $(C_{6-10})$aryl$(C_{1-8})$alkyl-, $(C_{5-10})$heteroaryl, $(C_{5-10})$heteroaryl$(C_{1-8})$alkyl-, —$(C_{2-4})_q$—$(CH_2)_{2-4}$—$X^1$, —$C(O)R^6$, —$CO_2R^6$, —$C(O)NR^7R^8$ or —$S(O)_2$—$NR^7R^8$; or $R^4$ and $R^5$ together with the atoms to which they are attached form a saturated or partially unsaturated, mono-, bicyclic- or aromatic ring having 3, 4, 5, 6, 7 or 8, ring atoms and optionally consisting of 1, 2, 3 or 4 heteroatoms selected from non-peroxide oxy, —S—, sulfinyl, sulfonyl and —NH— in the ring, and wherein the ring is optionally substituted with 1, 2, 3 or 4 substituents independently selected from halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COOR^b$ and —$C(O)NR^bR^c$;
- $R^6$ is hydrogen, $(C_{1-8})$alkyl, $R^bO(C_{1-8})$alkyl, $R^bR^cN(C_{1-8})$alkyl, halo$(C_{1-8})$alkyl, $(C_{3-10})$heterocyclyl, $(C_{3-10})$heterocyclyl$(C_{1-8})$alkyl-, $(C_{6-10})$aryl, $(C_{6-10})$aryl$(C_{1-8})$alkyl-, $(C_{4-10})$heteroaryl or $(C_{4-10})$heteroaryl$(C_{1-8})$alkyl-; wherein the heterocyclyl, heteroaryl or aryl are optionally substituted with 1, 2, 3 or 4 substituents independently selected from halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, $(C_{1-8})$alkyl, halo$(C_{1-8})$alkyl, —$NR^bR^c$, —$C(O)R^b$, —$COOR^b$ and —$C(O)NR^bR^c$;
- wherein $R^7$ and $R^8$ are independently hydrogen, $(C_{1-8})$alkyl, $R^aO(C_{1-8})$alkyl, $R^bR^cN(C_{1-8})$alkyl, halo$(C_{1-8})$alkyl, $(C_{3-10})$heterocyclyl, $(C_{6-10})$aryl, $(C_{6-10})$aryl$(C_{1-8})$ alkyl-, (C$_{4-10}$)heteroaryl; —COOR$^b$, —C(O)R$^b$ or —C(O)NR$^b$R$^c$ wherein the heterocyclyl, heteroaryl or aryl are optionally substituted with 1, 2, 3 or 4 substituents independently selected from halo, hydroxy, cyano, nitro, —OR$^a$, —SR$^a$, (C$_{6-10}$)aryl, —O(C$_{6-10}$)aryl, hydroxy(C$_{1-8}$)alkyl, R$^b$R$^c$N(C$_{1-8}$)alkyl, halo(C$_{1-8}$)alkyl, —NR$^b$R$^c$, —C(O)R$^b$, —COOR$^b$ and —C(O)NR$^b$R$^c$; or R$^7$ and R$^8$ together with the atoms to which they are attached form a saturated or partially unsaturated, mono-, bicyclic- or aromatic ring having 3, 4, 5, 6, 7 or 8, ring atoms optionally ring having from 4 to eight ring atoms and optionally consisting of 1, 2, 3 or 4 heteroatoms selected from non-peroxide oxy, —S—, sulfinyl, sulfonyl or —N(R$^b$)— in the ring;

X$^1$ is —OR$^6$, —C(O)R$^6$, —CO$_2$R$^6$ or —NR$^7$R$^8$; and

Y is oxy, —S—, sulfinyl, sulfonyl and —NH—; and q is 1, 2, 3 or 4.

24. The compound according to claim 1, wherein the alkyl, alkenyl, cycloalkyl, alkynyl, aryl, heterocyclyl or heteroaryl groups are unsubstituted or further substituted with one or more substituents independently selected from halo, hydroxy, cyano, nitro, —OR$^a$, —SR$^a$, (C$_{6-10}$)aryl, —O(C$_{6-10}$)aryl, hydroxy(C$_{1-8}$)alkyl, R$^b$R$^c$N(C$_{1-8}$)alkyl, halo(C$_{1-8}$)alkyl, —NR$^b$R$^c$, —N(CO)R$^b$, —C(O)R$^b$, —COOR$^b$ and —C(O)NR$^b$R$^c$; wherein R$^a$ is hydrogen, or (C$_{1-6}$)alkyl; and R$^b$ and R$^c$ are each independently hydrogen, (C$_{1-6}$)alkyl, (C$_{1-6}$)alkoxy, (C$_{3-8}$)cycloalkyl, (C$_{1-6}$)alkylthio, (C$_{6-10}$)aryl, (C$_{6-10}$)aryl(C$_{1-6}$)alkyl-, heteroaryl or heteroaryl(C$_{1-6}$)alkyl-; or R$^b$ and R$^c$ together with the nitrogen to which they are attached, form a pyrrolidyl, piperidyl, piperazinyl, azepinyl, diazepinyl, morpholinyl or thiomorpholinyl ring.

25. The compound according to claim 1, wherein R is hydrogen or is selected from the group consisting of methyl, ethyl, allyl, propargyl, i-propyl, n-propyl, n-butyl, i-butyl and halo(C$_{1-4}$)alkyl.

26. The compound according to claim 1, wherein R is selected from the group consisting of methyl, ethyl, —CH$_2$—CH$_2$—Cl, —CH$_2$—CH$_2$—Br and —CH$_2$—CH$_2$—CH$_2$—F.

27. The compound according to claim 1, wherein R$^1$ is hydrogen or is selected from the group consisting of (C$_{1-4}$)alkyl, (C$_{3-4}$)alkenyl, (C$_{3-8}$)alkenyl(C$_{1-8}$)alkyl, (C$_{3-8}$)alkynyl, (C$_{3-8}$)alkynyl(C$_{1-8}$)alkyl, (C$_{1-8}$)alkoxy, (C$_{3-8}$)cycloalkyl, (C$_{3-8}$)cycloalkyl(C$_{1-8}$)alkyl-, hydroxy(C$_{3-8}$)cycloalkyl(C$_{1-8}$)alkyl-, phenyl and phenyl(C$_{1-4}$)alkyl.

28. The compound according to claim 1, wherein R$^1$ is hydrogen or is selected from the group consisting of (C$_{3-6}$)cycloalkyl, (C$_{3-8}$)alkenyl(C$_{1-8}$)alkyl, (C$_{3-8}$)alkynyl(C$_{1-8}$)alkyl, hydroxy(C$_{3-8}$)cycloalkyl(C$_{1-8}$)alkyl- and (C$_{3-6}$)cycloalkyl(C$_{1-4}$) alkyl-.

29. The compound according to claim 1, wherein R$^1$ is selected from the group consisting of cyclopropyl, cyclopropylmethyl, cyclobutyl, hydroxycyclobutyl, trihalomethylcyclobutyl and cyclopentyl.

30. The compound according to claim 1, wherein R$^1$ is selected from the group consisting of methyl, ethyl, allyl, propargyl, i-propyl, n-propyl, n-butyl, i-butyl, phenyl, phenethyl, benzyl and (methoxyphenyl)ethyl.

31. The compound according to claim 1, wherein R$^1$ is selected from the group consisting of ethyl, n-propyl and allyl.

32. The compound according to claim 1, wherein R$^2$ is hydrogen or is selected from the group consisting of (C$_{1-4}$)alkyl, halo(C$_{1-8}$)alkyl, (C$_{3-4}$alkenyl, (C$_{3-4}$)alkynyl, phenyl, phenyl(C$_{1-4}$)alkyl and (methoxyphenyl)ethyl.

33. The compound according to claim 1, wherein R$^2$ is (C$_{3-6}$)cycloalkyl, halo(C$_{1-8}$)alkyl, or (C$_{3-6}$)cycloalkyl(C$_{1-4}$)alkyl-.

34. The compound according to claim 1, wherein R$^2$ is selected from the group consisting of cyclopropyl or cyclopropylmethyl, cyclobutyl, hydroxycyclobutyl, trihalomethylcyclobutyl and cyclopentyl.

35. The compound according to claim 1, wherein R$^2$ is selected from the group consisting of methyl, ethyl, allyl, propargyl, i-propyl, n-propyl, n-butyl, i-butyl, phenyl, phenethyl, trifluoromethylmethyl, fluoroethyl and benzyl.

36. The compound according to claim 1, wherein R is hydrogen or is selected from the group consisting of methyl, ethyl, allyl, propargyl, i-propyl, n-propyl, n-butyl, i-butyl and halo(C$_{1-4}$)alkyl;

one of R$^1$ and R$^2$ is selected from the group consisting of cyclopropyl, and cyclopropylmethyl; and, the other of R$^1$ and R$^2$ is hydrogen or selected from the group consisting of methyl, ethyl, allyl, propargyl, i-propyl, n-propyl, cyclopropyl, cyclopropylmethyl, n-butyl, i-butyl, phenyl, phenethyl and benzyl.

37. The compound according to claim 1, wherein R is selected from the group consisting of methyl, ethyl, —CH$_2$—CH$_2$—Cl, —CH$_2$—CH$_2$—Br and —CH$_2$—CH$_2$—CH$_2$—F;

one of R$^1$ and R$^2$ is selected from the group consisting of cyclopropyl, cyclopropylmethyl, cyclobutyl, hydroxycyclobutyl, trihalomethylcyclobutyl, cyclopentyl; and, the other of R$^1$ and R$^2$ is hydrogen or selected from the group consisting of methyl, ethyl, allyl, propargyl, i-propyl, n-propyl, cyclopropyl, cyclopropylmethyl, (methoxyphenyl)ethyl, cyclobutyl, hydroxycyclobutyl, trihalomethylcyclobutyl, cyclopentyl, trifluoromethylmethyl and fluoroethyl.

38. The compound according to claim 1, wherein Z$^1$ is substituted by a substituent selected from the group consisting of —OH, —O(C$_{1-4}$)alkyl, —OC(O)NR$^7$R$^8$, (C$_{1-4}$)alkyl, —NR$^4$R$^5$, F, Cl, Br, I, nitro, cyano, trifluoromethyl, —CO$_2$R$^6$ and —NC(O)R$^6$;

R$^4$ and R$^5$ are each independently hydrogen or are selected from the group consisting of (C$_{1-6}$)alkyl, (C$_{3-6}$)cycloalkyl, (C$_{3-6}$)heterocyclyl, (C$_{6-10}$)aryl, (C$_{7-12}$)aralkyl, (C$_{5-6}$)heteroaryl, or (C$_{5-6}$)heteroaryl(C$_{1-4}$)alkyl, —S(O$_2$)NH$_2$, —C(O)R$^6$, —CO$_2$R$^6$ and —C(O)NR$^6$R$^7$;

R$^6$ is hydrogen, (C$_{1-8}$)alkyl, R$^b$O(C$_{1-8}$)alkyl, R$^b$R$^c$N(C$_{1-8}$)alkyl, halo(C$_{1-8}$)alkyl, (C$_{3-10}$)heterocyclyl, (C$_{3-10}$)heterocyclyl(C$_{1-8}$)alkyl-, (C$_{6-10}$)aryl, (C$_{6-10}$)aryl(C$_{1-8}$)alkyl-, (C$_{4-10}$)heteroaryl or (C$_{4-10}$)heteroaryl(C$_{1-8}$)alkyl-; wherein the heterocyclyl, heteroaryl or aryl are optionally substituted with 1, 2, 3 or 4 substituents independently selected from halo, hydroxy, cyano, nitro, —OR$^a$, —SR$^a$, (C$_{6-10}$)aryl, —O(C$_{6-10}$)aryl, hydroxy (C$_{1-8}$)alkyl, R$^b$R$^c$N(C$_{1-8}$)alkyl, (C$_{1-8}$)alkyl, halo(C$_{1-8}$)alkyl, —NR$^b$R$^c$, —C(O)R$^b$, —COOR$^b$ and —C(O)NR$^b$R$^c$;

R$^7$ and R$^8$ are each independently hydrogen, (C$_{1-8}$)alkyl, R$^b$O(C$_{1-8}$)alkyl, R$^b$R$^c$N(C$_{1-8}$)alkyl, halo(C$_{1-8}$)alkyl, (C$_{3-10}$)heterocyclyl, (C$_{6-10}$)aryl, (C$_{6-10}$)aryl(C$_{1-8}$)alkyl-, (C$_{4-10}$)heteroaryl; —COOR$^b$, —C(O)R$^b$ or —C(O)NR$^b$R$^c$ wherein the heterocyclyl, heteroaryl or aryl are optionally substituted with 1, 2, 3 or 4 substituents independently selected from halo, hydroxy, cyano, nitro, —OR$^a$, —SR$^a$, (C$_{6-10}$)aryl, —O(C$_{6-10}$)aryl, hydroxy(C$_{1-8}$)alkyl, R$^b$R$^c$N(C$_{1-8}$)alkyl, halo(C$_{1-8}$)alkyl, —NR$^b$R$^c$, —C(O)R$^b$, —COOR$^b$ and —C(O)NR$^b$R$^c$; or R$^7$ and R$^8$ together with the atoms to which they are attached form a saturated or partially unsaturated, mono-, bicyclic- or aromatic ring having 3, 4, 5, 6, 7 or 8, ring atoms optionally ring having from 4 to eight ring atoms and optionally consisting of 1, 2, 3 or 4 heteroatoms selected from non-peroxide oxy, —S—, sulfinyl, sulfonyl or NH in the ring.

39. The compound of claim 38, wherein $Z^1$ is substituted by one —$NR^4R^5$.

40. The compound of claim 39, wherein $R^4$ and $R^5$ together with the nitrogen to which they are attached, form a pyrrolidyl, piperidyl, piperazinyl, azepinyl, diazepinyl, morpholinyl or thiomorpholinyl ring, wherein the ring is unsubstituted or substituted with 1, 2, 3 or 4 substituents independently selected from halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COOR^b$ and —$C(O)NR^bR^c$
    wherein $R^a$ is hydrogen, or $(C_{1-6})$alkyl; and $R^b$ and $R^c$ are each independently hydrogen, or are selected from the group consisting of $(C_{1-6})$alkyl, $(C_{1-6})$alkoxy, $(C_{3-8})$cycloalkyl, $(C_{1-6})$alkylthio, $(C_{6-10})$aryl, $(C_{6-10})$aryl$(C_{1-6})$alkyl-, heteroaryl or heteroaryl$(C_{1-6})$alkyl-; or $R^b$ and $R^c$ together with the nitrogen to which they are attached form a pyrrolidyl, piperidyl, piperazinyl, azepinyl, diazepinyl, morpholinyl or a thiomorpholinyl ring.

41. The compound of claim 39, wherein $R^4$ and $R^5$ are each independently hydrogen or are independently selected from the group consisting of $(C_{1-4})$alkyl, hydroxy$(C_{2-4})$alkyl, $(C_{3-6})$cycloalkyl, $(C_{6-10})$aryl, $(C_{7-10})$aralkyl, $(C_{5-6})$heteroaryl, —$(CH_2$—$CH_2$—$O)_q$—$(CH_2$—$CH_2)$—$OR^b$, —$(CH_2$—$CH_2$—$O)_q$—$(CH_2$—$CH_2)$—$COOR^b$, —$(CH_2$—$CH_2$—$O)_q$—$(CH_2$—$CH_2)$—$NR^bR^c$, —$NR^7R^8$, —$C(O)R^6$, —$CO_2R^6$ and —$C(O)NR^7R^8$
    wherein $R^b$ and $R^c$ are each independently hydrogen, or are selected from the group consisting of $(C_{1-6})$alkyl, $(C_{1-6})$alkoxy, $(C_{3-8})$cycloalkyl, $(C_{1-6})$alkylthio, $(C_{6-10})$aryl, $(C_{6-10})$aryl$(C_{1-6})$alkyl-, heteroaryl or heteroaryl$(C_{1-6})$alkyl-; or $R^b$ and $R^c$ together with the nitrogen to which they are attached form a pyrrolidyl, piperidyl, piperazinyl, azepinyl, diazepinyl, morpholinyl or a thiomorpholinyl ring; and,
    and q is 1, 2, 3 or 4.

42. The compound of claim 39, wherein $R^4$ and $R^5$ are each independently selected from the group consisting of methyl, ethyl, propyl, pentyl, hydroxyethyl, hydroxypropyl, ethoxyethyl, diethoxyethyl, methylbenzyl, aminomethylbenzyl, methoxybenzyl, methoxyphenethyl, furylmethyl, cyclopentyl, cyclohexyl, thiophenyl, —$C(O)R^6$, —$CO_2R^6$ and —$C(O)NHR^7$.

43. The compound according to claim 1, wherein:
    R is hydrogen, methyl or ethyl;
    one of $R^1$ and $R^2$ is selected from the group consisting of cyclopropyl, cyclopropylmethyl, cyclobutyl, hydroxycyclobutyl, trihalomethylcyclobutyl, and cyclopentyl;
    the other of $R^1$ and $R^2$ is selected from the group consisting of methyl, ethyl, allyl, propargyl, i-propyl, n-propyl, cyclopropyl, cyclopropylmethyl, n-butyl, cyclobutyl, hydroxycyclobutyl, trihalomethylcyclobutyl, cyclopentyl, trifluoromethylmethyl, fluoroethyl and i-butyl; and
    $Z^1$ is $(C_{4-10})$heterocyclyl wherein the heterocyclyl is unsubstituted or substituted with 1, 2 3 or 4 substituents independently selected from halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COOR^b$ and —$C(O)NR^bR^c$
    wherein $R^a$ is hydrogen, or $(C_{1-6})$alkyl; and $R^b$ and $R^c$ are each independently hydrogen, or are selected from the group consisting of $(C_{1-6})$alkyl, $(C_{1-6})$alkoxy, $(C_{3-8})$cycloalkyl, $(C_{1-6})$alkylthio, $(C_{6-10})$aryl, $(C_{6-10})$aryl$(C_{1-6})$alkyl-, heteroaryl or heteroaryl$(C_{1-6})$alkyl-; or $R^b$ and $R^c$ together with the nitrogen to which they are attached form a pyrrolidyl, piperidyl, piperazinyl, azepinyl, diazepinyl, morpholinyl or a thiomorpholinyl ring.

44. The compound according to claim 1, wherein each substituent is independently selected from the group consisting of —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$N(CO)R^b$, —$C(O)R^b$, —$COOR^b$ and —$C(O)NR^bR^c$;
    wherein $R^a$ is hydrogen, or $(C_{1-6})$alkyl; and $R^b$ and $R^c$ are each independently hydrogen, or are selected from the group consisting of$(C_{1-6})$alkyl, $(C_{1-6})$alkoxy, $(C_{3-8})$cycloalkyl, $(C_{1-6})$alkylthio, $(C_{6-10})$aryl, $(C_{6-10})$aryl$(C_{1-6})$alkyl-, heteroaryl or heteroaryl$(C_{1-6})$alkyl-; or $R^b$ and $R^c$ together with the nitrogen to which they are attached form a pyrrolidyl, piperidyl, piperazinyl, azepinyl, diazepinyl, morpholinyl or a thiomorpholinyl ring.

45. The compound according to claim 1, wherein Z and $Z^1$ are substituted by at least one substituent selected from the group consisting of —$OR^3$, —$SR^3$, halo, hydroxy, —$S(O)$—$NR^4R^5$, —$S(O)_2$—$NR^4R^5$, —$NR^4R^5$ and $(C_{4-10})$heterocyclyl wherein the heterocyclyl is unsubstituted or substituted with 1, 2, 3 or 4 substituents independently selected from halo, hydroxy, cyano, nitro, —$OR^a$, —$SR^a$, $(C_{1-8})$alkyl, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COR^b$ and —$C(O)NR^bR^c$; wherein
    $R^3$ is selected from the group consisting of $(C_{1-8})$alkyl, $(C_{3-8})$alkenyl, $(C_{3-8})$alkynyl, $(C_{6-10})$aryl, $(C_{6-10})$aryl$(C_{1-8})$alkyl-, $(C_{5-10})$heteroaryl, $(C_{5-10})$heteroaryl$(C_{1-8})$alkyl-, —$CO_2R^6$ and —$C(O)NR^7R^8$;
    $R^4$ and $R^5$ are each independently hydrogen, or are each independently selected from the group consisting of $(C_{1-8})$alkyl, $(C_{3-8})$alkenyl, $(C_{3-8})$alkynyl, $(C_{1-8})$alkoxy, $(C_{3-8})$cycloalkyl, $(C_{3-8})$cycloalkyl$(C_{1-8})$alkyl-, $(C_{6-10})$polycycloalkyl, $(C_{6-18}$ is)polycycloalkyl$(C_{1-8})$alkyl-, $(C_{3-10})$heterocyclyl, $(C_{3-10})$heterocyclyl$(C_{1-8})$alkyl-, —$NR^7R^8$, $(C_{6-10})$aryl, $(C_{6-10})$aryl$(C_{1-8})$alkyl-, $(C_{5-10})$heteroaryl, $(C_{5-10})$heteroaryl$(C_{1-8})$alkyl-, —$(C_{2-4}$—$Y)_q$ —$(CH_2)_{2-4}$—$X^1$, —$C(O)R^6$, —$CO_2R^6$, —$C(O)NR^7R^8$ and —$S(O)_2$—$NR^7R^8$; or $R^4$ and $R^5$ together with the atoms to which they are attached form a saturated or partially unsaturated, mono-, bicyclic- or aromatic ring having 3, 4, 5, 6, 7 or 8, ring atoms and optionally consisting of 1, 2, 3 or 4 heteroatoms selected from non-peroxide oxy, —S—, sulfinyl, sulfonyl and —$N(R^9)$—in the ring, and wherein the ring is unsubstituted or substituted with 1, 2, 3 or 4 substituents independently selected from halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$C(O)R^b$, —$COOR^b$ and —$C(O)NR^bR^c$;
    $X^1$ is —$OR^6$, —$C(O)R^6$, —$C_2R^{b\ 6}$ or —$NR^7R^8$; and Y is oxy, —S—, sulfinyl, sulfonyl and —$N(R^9)$—;
    wherein the alkyl, alkenyl, cycloalkyl, alkynyl, aryl, heterocyclyl or heteroaryl groups of $R^1$, $R^2$, $R^3$, $R^4$ and $R^5$ groups are unsubstituted or substituted with one or more substituents independently selected from the group consisting of halo, hydroxy, cyano, nitro, —$OR^a$, —$SR^a$, $(C_{6-10})$aryl, —$O(C_{6-10})$aryl, hydroxy$(C_{1-8})$alkyl, $R^bR^cN(C_{1-8})$alkyl, halo$(C_{1-8})$alkyl, —$NR^bR^c$, —$N(CO)R^b$, —$C(O)R^b$, —$COOR^b$ and —$C(O)NR^bR^c$;
    wherein $R^6$ is hydrogen, or is selected from the group consisting of $(C_{1-8})$alkyl, $R^bO(C_{1-8})$alkyl, $R^bR^cN(C_{1-8})$alkyl, halo$(C_{1-8})$alkyl, $(C_{3-10})$heterocyclyl, $(C_{3-10})$heterocyclyl$(C_{1-8})$alkyl-, $(C_{6-10})$aryl, $(C_{6-10})$aryl$(C_{1-8})$alkyl-, $(C_{4-10})$heteroaryl and $(C_{4-10})$heteroaryl$(C_{1-8})$ alkyl-; wherein the heterocyclyl, heteroaryl or aryl are unsubstituted or substituted with 1, 2, 3, or 4 substituents independently selected from halo, hydroxy, cyano, nitro, —OR$^a$, —SR$^a$, (C$_{6-10}$)aryl, —O(C$_{6-10}$)aryl, hydroxy(C$_{1-8}$)alkyl, R$^b$R$^c$N(C$_{1-8}$)alkyl, (C$_{1-8}$)alkyl, halo(C$_{1-8}$)alkyl, —NR$^b$R$^c$, —C(O)R$^b$, —COOR$^b$ and —C(O)NR$^b$R$^c$;

wherein R$^7$, R$^8$ and R$^9$ are each independently hydrogen, or are each independently selected from the group consisting of (C$_{1-8}$)alkyl, R$^b$O(C$_{1-8}$)alkyl, R$^b$R$^c$N(C$_{1-8}$)alkyl, halo(C$_{1-8}$)alkyl, (C$_{3-10}$)heterocyclyl, (C$_{6-10}$)aryl, (C$_{6-10}$)aryl(C$_{1-8}$)alkyl-, (C$_{4-10}$)heteroaryl; —COOR$^b$, —C(O)R$^b$ or —C(O)NR$^b$R$^c$ wherein the heterocyclyl, heteroaryl or aryl are unsubstituted or substituted with 1, 2, 3, or 4 substituents independently selected from halo, hydroxy, cyano, nitro, —OR$^a$, —SR$^a$, (C$_{6-10}$)aryl, —O(C$_{6-10}$)aryl, hydroxy(C$_{1-8}$)alkyl, R$^b$R$^c$N(C$_{1-8}$)alkyl, halo(C$_{1-8}$)alkyl, —NR$^b$R$^c$, —C(O)R$^b$, —COOR$^b$ and —C(O)NR$^b$R$^c$; or R$^7$ and R$^8$ together with the atoms to which they are attached form a saturated or partially unsaturated, mono-, bicyclic or aromatic ring having 3, 4, 5, 6, 7 or 8 ring atoms and optionally consisting of 1, 2, 3 or 4 heteroatoms selected from non-peroxide oxy, —S—, sulfinyl, sulfonyl or —N(R$^b$)— in the ring;

R$^a$ is hydrogen or (C$_{1-6}$)alkyl; and R$^b$ and R$^c$ are each independently hydrogen, or are selected from the group consisting of (C$_{1-6}$)alkyl, (C$_{1-6}$)alkoxy, (C$_{3-8}$)cycloalkyl, (C$_{1-6}$)alkylthio, (C$_{6-10}$)aryl, (C$_{6-10}$)aryl(C$_{1-6}$)alkyl-, heteroaryl or heteroaryl(C$_{1-6}$)alkyl-, or R$^b$ and R$^c$ together with the nitrogen to which they are attached form a pyrrolidyl, piperidyl, piperazinyl, azepinyl, diazepinyl, morpholinyl or thiomorpholinyl ring; and q is 1, 2, 3 or 4; or a pharmaceutically acceptable salt thereof.

46. The compound according to claim 1, wherein the alkyl, alkenyl, cycloalkyl, alkynyl, aryl, heterocyclyl or heteroaryl groups are unsubstituted or substituted with one or more substituents independently selected from the group consisting of (C$_{1-5}$)alkyl, (C$_{1-5}$)alkoxy, aryloxy, heteroaryloxy, amino, halo, hydroxy, cyano, and nitro groups.

47. The compound according to claim 1, wherein the substituent on Z$^1$ is selected from the group consisting of:

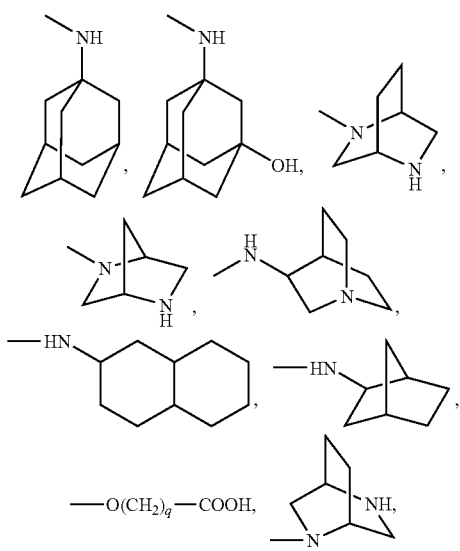

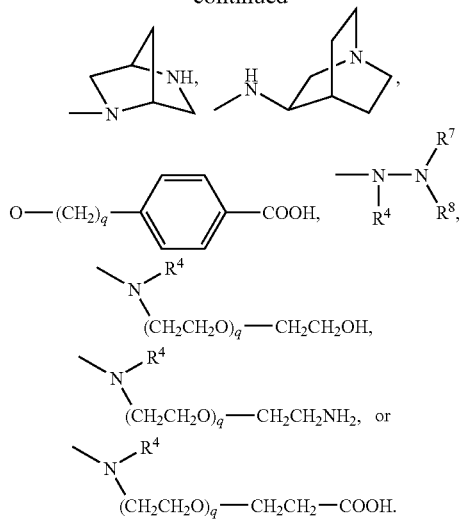

R$^4$ is hydrogen or selected from the group consisting of (C$_{1-8}$)alkyl, halo(C$_{1-8}$)alkyl, (C$_{1-8}$)alkylC(O)—, (C$_{3-8}$)alkenyl, (C$_{3-8}$)alkynyl, (C$_{3-6}$)cycloalkyl(C$_{1-8}$)alkyl-, (C$_{4-10}$)heterocyclyl, (C$_{4-10}$)heterocyclyl(C$_{1-8}$)alkyl-, (C$_{6-10}$)aryl(C$_{1-8}$)alkyl-, and (C$_{5-10}$)heteroaryl(C$_{1-8}$)alkyl-;

R$^7$ and R$^8$ are each independently hydrogen, (C$_{1-8}$)alkyl, R$^b$O(C$_{1-8}$)alkyl, R$^b$R$^c$N(C$_{1-8}$)alkyl, halo(C$_{1-8}$)alkyl, (C$_{3-10}$)heterocyclyl, (C$_{6-10}$)aryl, (C$_{6-10}$)aryl(C$_{1-8}$)alkyl-, (C$_{4-10}$)heteroaryl; —COOR$^b$, —C(O)R$^b$ or —C(O)NR$^b$R$^c$ wherein the heterocyclyl, heteroaryl or aryl are optionally substituted with 1, 2, 3 or 4 substituents independently selected from halo, hydroxy, cyano, nitro, —OR$^a$, —SR$^a$, (C$_{6-10}$)aryl, —O(C$_{6-10}$)aryl, hydroxy(C$_{1-8}$)alkyl, R$^b$R$^c$N(C$_{1-8}$)alkyl, halo(C$_{1-8}$)alkyl, —NR$^b$R$^c$, —C(O)R$^b$, —COOR$^b$ and —C(O)NR$^b$R$^c$; or R$^7$ and R$^8$ together with the atoms to which they are attached form a saturated or partially unsaturated, mono-, bicyclic- or aromatic ring having 3, 4, 5, 6, 7 or 8, ring atoms optionally ring having from 4 to eight ring atoms and optionally consisting of 1, 2, 3 or 4 heteroatoms selected from non-peroxide oxy, —S—, sulfinyl, sulfonyl or —NH— in the ring;

R$^a$ is hydrogen, or (C$_{1-6}$)alkyl; R$^b$ and R$^c$ are each independently hydrogen, (C$_{1-6}$)alkyl, (C$_{1-6}$)alkoxy, (C$_{3-8}$)cycloalkyl, (C$_{1-6}$)alkylthio, (C$_{6-10}$)aryl, (C$_{6-10}$)aryl(C$_{1-6}$)alkyl-, heteroaryl or heteroaryl(C$_{1-6}$)alkyl-; or R$^b$ and R$^c$ together with the nitrogen to which they are attached, form a pyrrolidyl, piperidyl, piperazinyl, azepinyl, diazepinyl, morpholinyl or thiomorpholinyl ring;

and q is 1, 2, 3 or 4.

48. The compound according to claim 1, wherein -Z$^1$ is selected from the group consisting of:

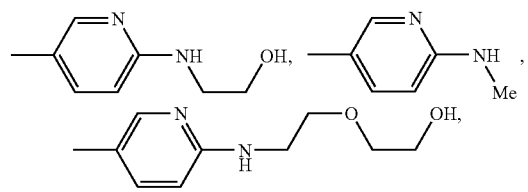

-continued
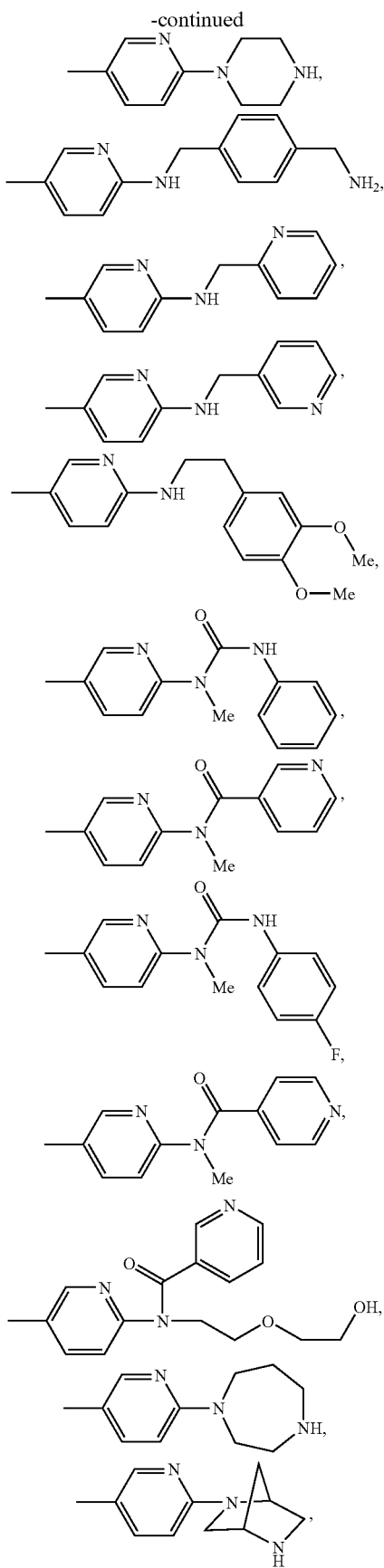
-continued
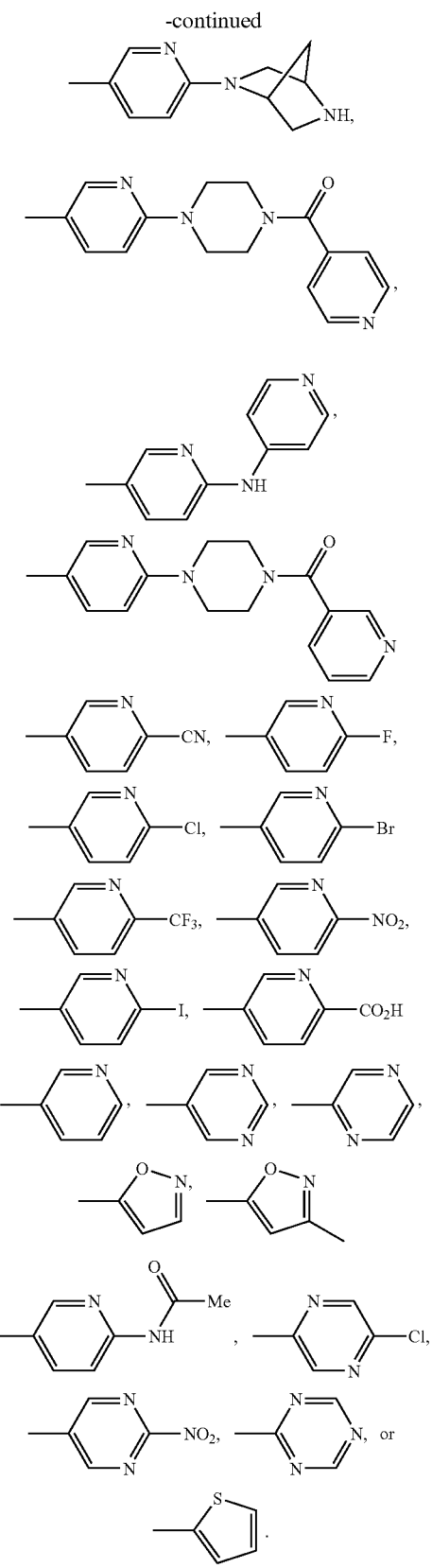
49. The compound according to claim 1, wherein $R^1$ is cyclopropyl, $R^2$ is n-propyl; R is hydrogen and m is zero.

50. The compound of claim 1, wherein -Z(L¹)$_n$-Z¹ comprises the formula:
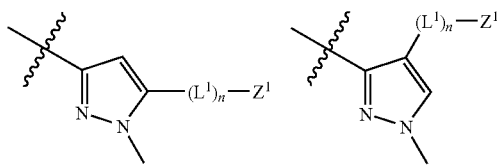
where n is 1.
51. The compound according to claim 1, wherein -Z¹ is selected from the group consisting of:
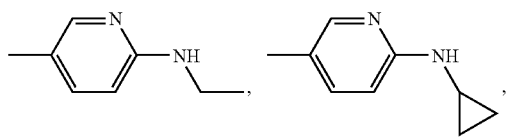
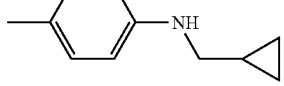
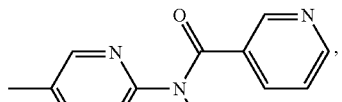
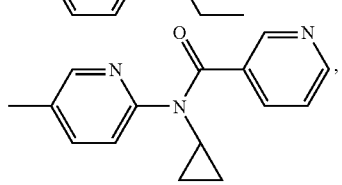
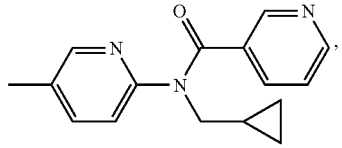
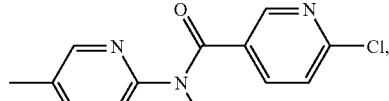
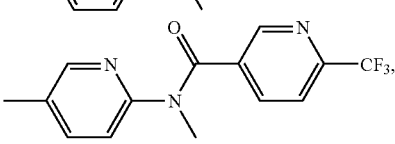
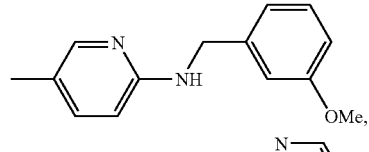
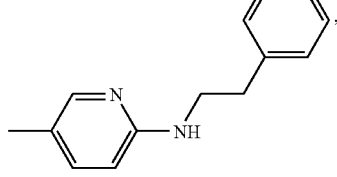
-continued
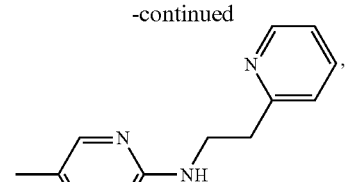
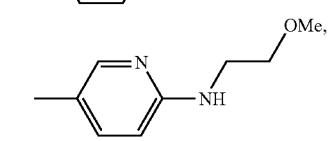
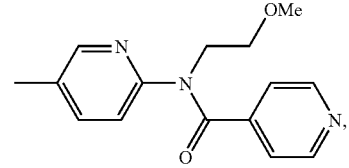
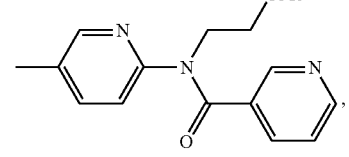
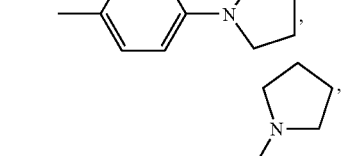
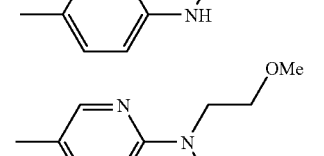
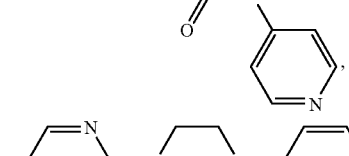
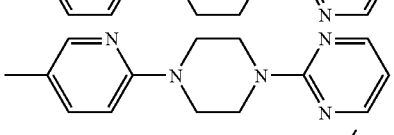
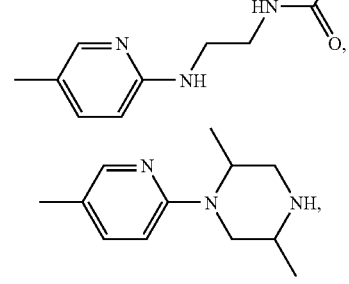

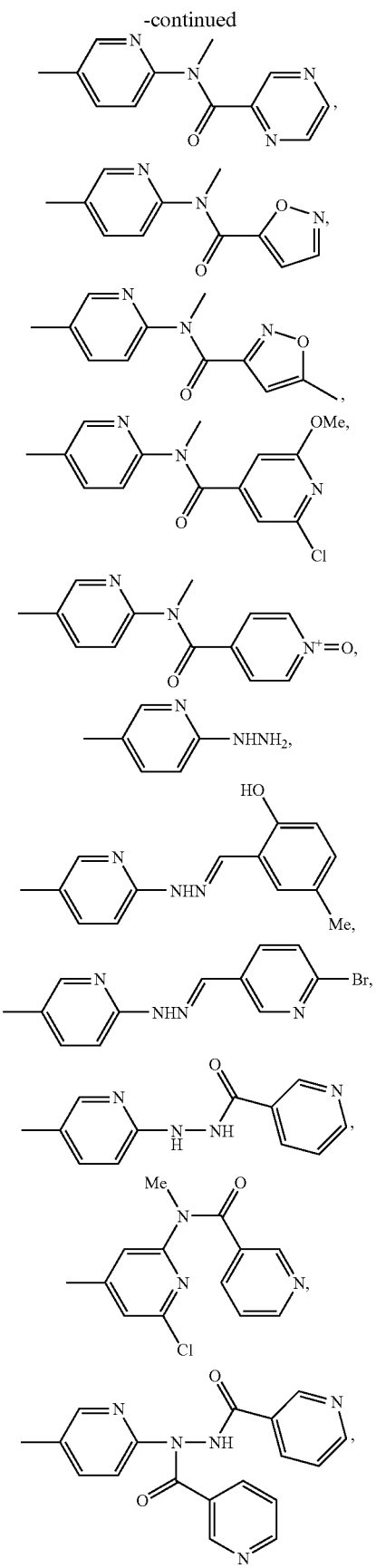

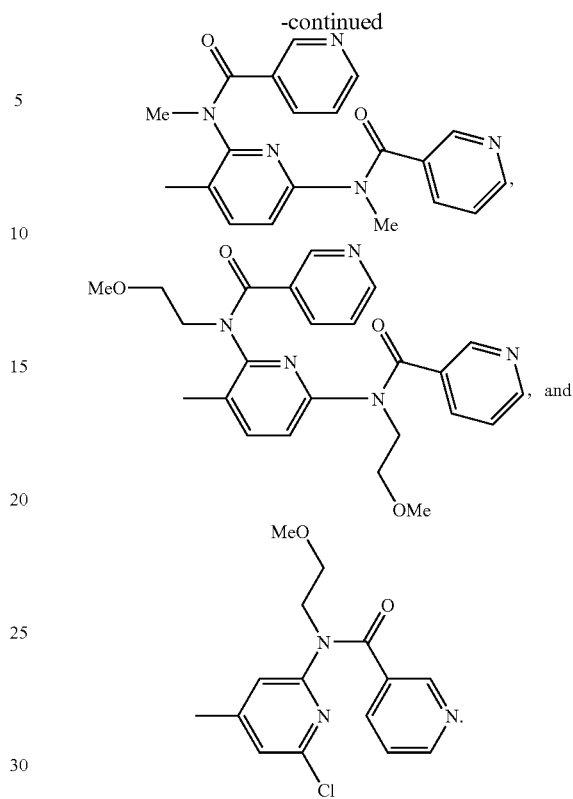

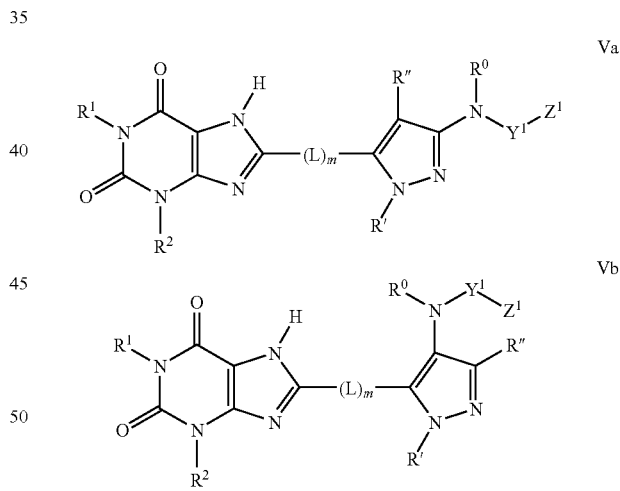

52. A compound of formula Va or formula Vb:

wherein:
R⁰ is selected from the group consisting of $(C_{1-4})$alkyl, halo$(C_{1-4})$alkyl, $(C_{3-8})$alkenyl, $(C_{3-8})$alkynyl, $(C_{1-4})$alkoxy $(C_{1-4})$alkyl, $R^4R^5N(C_{1-4})$alkyl-, $R^4R^5NC(O)(C_{1-4})$alkyl-, $(C_{3-6})$cycloalkyl, $(C_{3-6})$cycloalkyl$(C_{1-4})$alkyl-, $(C_{4-10})$heterocyclyl$(C_{1-4})$alkyl-, $(C_{6-10})$aryl$(C_{1-4})$alkyl-, and $(C_{5-10})$heteroaryl$(C_{1-8})$alkyl-, each substituted or unsubstituted;

R' is hydrogen or is selected from the group consisting of $(C_{1-4})$alkyl, halo$(C_{1-4})$alkyl, $(C_{3-8})$alkenyl, $(C_{3-8})$alkynyl, $(C_{1-4})$alkoxy, $(C_{3-8})$cycloalkyl, $(C_{3-8})$cycloalkyl$(C_{1-4})$alkyl-, $(C_{4-10})$heterocyclyl, $(C_{4-10})$heterocyclyl$(C_{1-4})$alkyl-, $(C_{6-10})$aryl, $(C_{6-10})$aryl$(C_{1-4})$alkyl-, ($C_{5-10}$)heteroaryl and ($C_{5-10}$) heteroaryl($C_{1-8}$)alkyl-, each substituted or unsubstituted;

R" is hydrogen or is selected from the group consisting of amino, cyano, halo, hydroxy, ($C_{1-8}$)alkyl, halo($C_{1-8}$)alkyl, ($C_{3-8}$)alkenyl, ($C_{3-8}$)alkynyl, ($C_{1-8}$)alkoxy, ($C_{3-8}$)cycloalkyl, ($C_{3-8}$)cycloalkoxy, aryloxy, heteroaryloxy, ($C_{3-8}$)cycloalkyl($C_{1-8}$)alkyl-, ($C_{4-10}$)heterocyclyl, ($C_{4-10}$)heterocyclyl($C_{1-8}$)alkyl-, ($C_{6-10}$)aryl, ($C_{6-10}$)aryl($C_{1-8}$)alkyl-, ($C_{5-10}$)heteroaryl and ($C_{5-10}$) heteroaryl($C_{1-8}$)alkyl-, each substituted or unsubstituted;

$R^1$ and $R^2$ are each independently hydrogen, or are each independently selected from the group consisting of substituted or unsubstituted ($C_{1-8}$)alkyl, halo($C_{1-8}$)alkyl, ($C_{3-8}$)alkenyl, ($C_{3-8}$)alkenyl($C_{1-8}$)alkyl, ($C_{3-8}$)alkynyl, ($C_{3-8}$)alkynyl($C_{1-8}$)alkyl, ($C_{1-8}$)alkoxy, ($C_{3-8}$)cycloalkyl, ($C_{3-8}$)cycloalkyl($C_{1-8}$)alkyl-, ($C_{4-10}$)heterocyclyl, ($C_{4-10}$)heterocyclyl($C_{1-8}$)alkyl-, ($C_{6-10}$)aryl, ($C_{6-10}$)aryloxy, ($C_{6-10}$)aryl($C_{1-8}$)alkyl-, ($C_{5-10}$)heteroaryl and ($C_{5-10}$)heteroaryl($C_{1-8}$)alkyl-;

$R^4$ and $R^5$ are each independently hydrogen, or are each independently selected from the group consisting of -($C_{1-8}$)alkyl, halo($C_{1-8}$)alkyl, alkylC(O)—, ($C_{3-8}$)alkenyl, ($C_{3-8}$)alkynyl, ($C_{3-6}$)cycloalkyl($C_{1-8}$)alkyl-, ($C_{4-10}$)heterocyclyl, ($C_{4-10}$)heterocyclyl($C_{1-8}$)alkyl-, ($C_{6-10}$)aryl($C_{1-8}$)alkyl-, and ($C_{5-10}$)heteroaryl($C_{1-8}$) alkyl-, or wherein $R^4$ and $R^5$ together with the nitrogen to which they attach form a 3-6 member heterocycle optionally interrupted by a O, S or N($C_{1-8}$)alkyl;

L a substituted or unsubstituted linker consisting of 1, 2, 3 or 4 linking atoms selected from the group consisting of carbon, nitrogen, oxygen, sulfur and phosphorus;

$Y^1$ is selected from the group consisting of —C(O)—, —S(O)— and —S(O)$_2$—; and $Z_1$ is selected from the group consisting of substituted or unsubstituted 3-pyridyl, 4-pyridyl, pyrazinyl or pyrimidinyl;

where m is 0 or 1; or a pharmaceutically acceptable salt thereof.

53. A compound selected from the group consisting of:

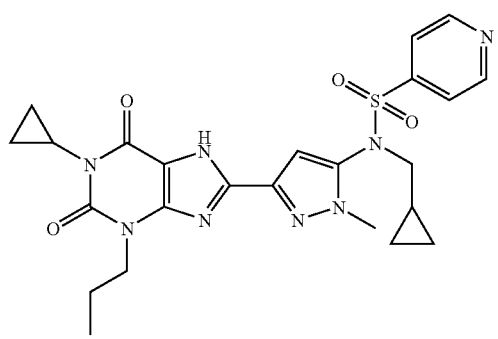

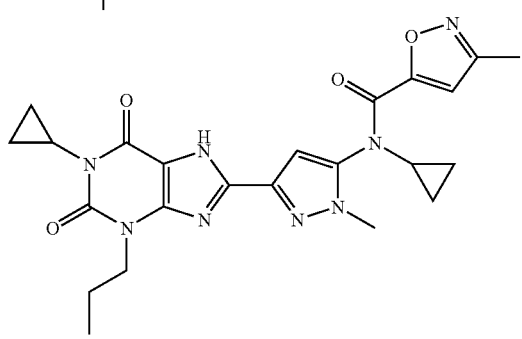

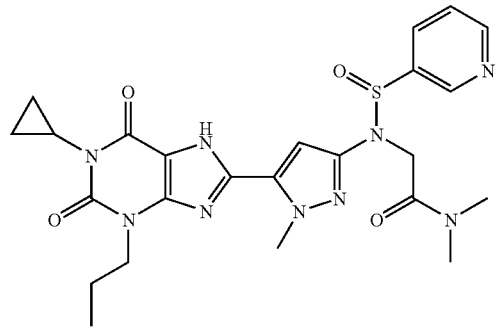

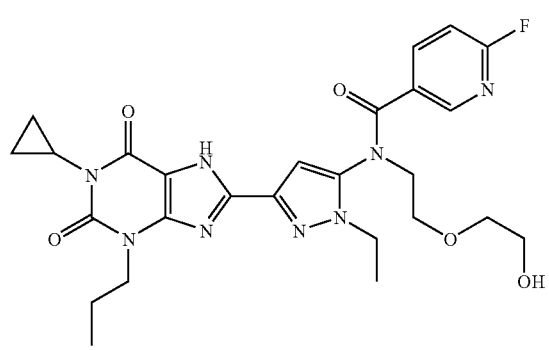

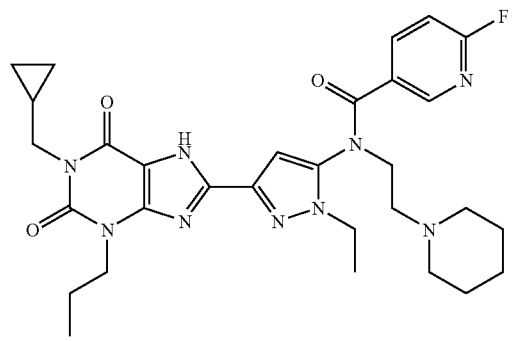

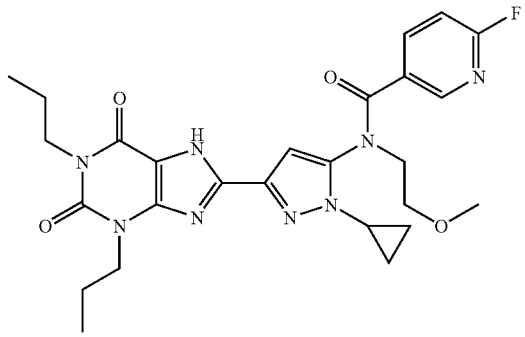

or a pharmaceutically acceptable salt thereof, optionally in the form of a single stereoisomer or mixture of stereoisomers thereof

54. The compound of claim 1 that is:
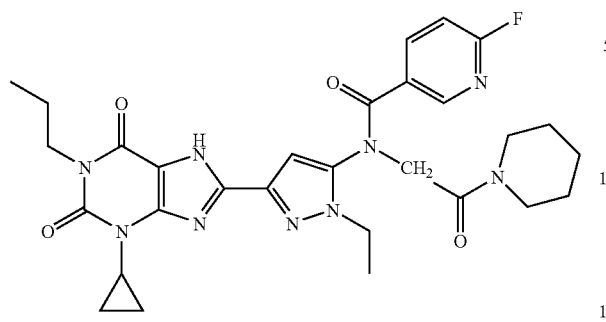
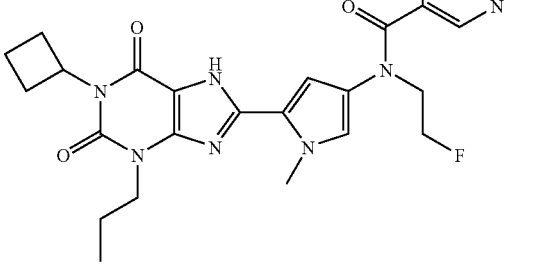
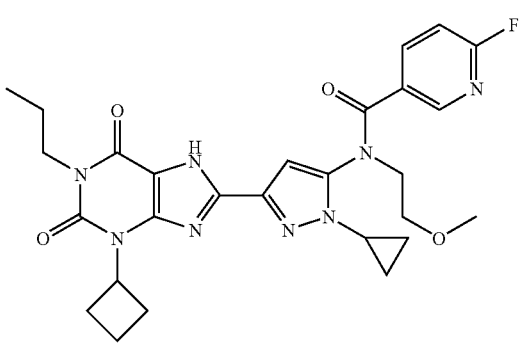
or a pharmaceutically acceptable salt thereof, optionally in the form of a single stereoisomer or mixture of stereoisomers thereof.
55. A compound of claim 1 selected from the group consisting of:
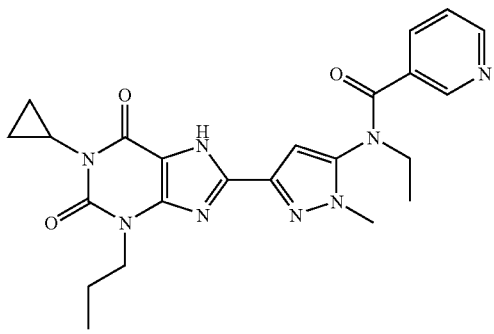
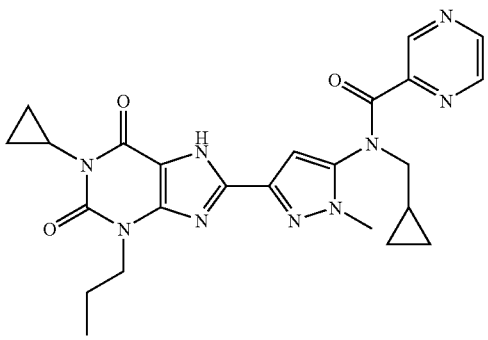
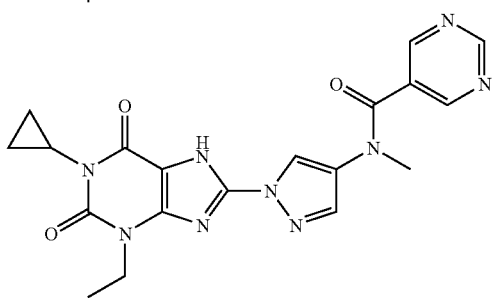
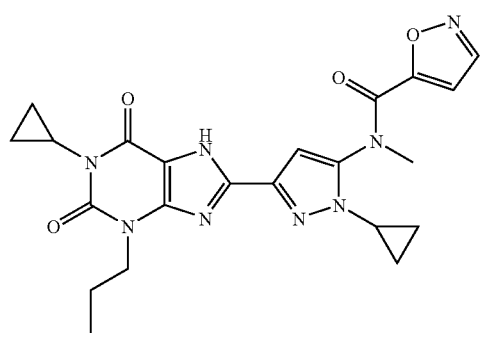
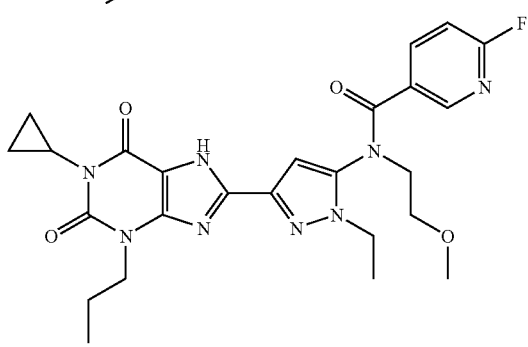
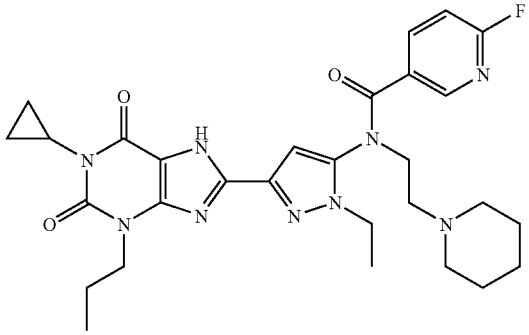

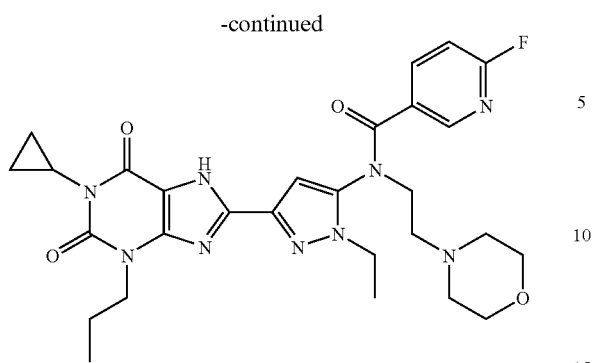

or a pharmaceutically acceptable salt thereof, optionally in the form of a single stereoisomer or mixture of stereoisomers thereof.

56. A selected from the group consisting of:

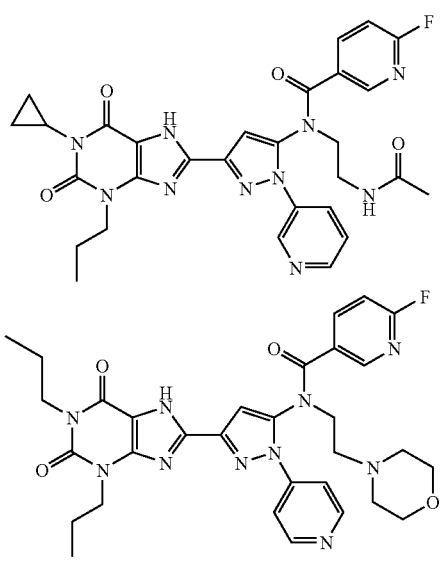

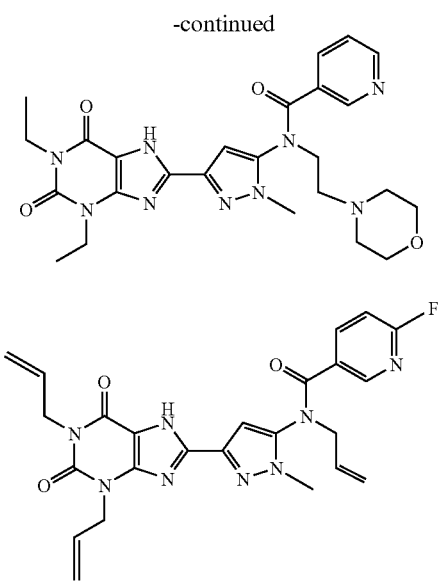

or a pharmaceutically acceptable salt thereof, optionally in the form of a single stereoisomer or mixture of stereoisomers thereof.

57. A pharmaceutical composition comprising:
(a) a therapeutically effective amount of a compound according to claim 1; and
(b) a pharmaceutically acceptable excipient.

58. A method for treating asthma comprising administering an effective amount of a compound according to claim 1 to a mammal in need of such treatment.

59. A method for improving insulin sensitivity, comprising administering an effective amount of a compound according to claim 1 or a pharmaceutically acceptable salt thereof to a mammal in need of such treatment.

* * * * *

UNITED STATES PATENT AND TRADEMARK OFFICE
CERTIFICATE OF CORRECTION

| | | |
|---|---|---|
| PATENT NO. | : 7,618,962 B2 | Page 1 of 1 |
| APPLICATION NO. | : 11/362393 | |
| DATED | : November 17, 2009 | |
| INVENTOR(S) | : Wang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 680 days.

Signed and Sealed this

Twenty-second Day of February, 2011

David J. Kappos
*Director of the United States Patent and Trademark Office*